US009468504B2

(12) United States Patent
Jung et al.

(10) Patent No.: US 9,468,504 B2
(45) Date of Patent: Oct. 18, 2016

(54) DENTAL CUTTING SYSTEM AND METHOD WITH REMOTE CUTTING GUIDE

(71) Applicant: DigitalPrep Technologies, Inc., West Valley City, UT (US)

(72) Inventors: Daniel Yonil Jung, Sandy, UT (US); Yunoh Jung, Sandy, UT (US)

(73) Assignee: B & D Dental Corporation, West Valley City, UT (US)

( * ) Notice: Subject to any disclaimer, the term of this patent is extended or adjusted under 35 U.S.C. 154(b) by 76 days.

(21) Appl. No.: 14/191,298

(22) Filed: Feb. 26, 2014

(65) Prior Publication Data

US 2014/0242541 A1 Aug. 28, 2014

Related U.S. Application Data

(60) Provisional application No. 61/770,248, filed on Feb. 27, 2013, provisional application No. 61/830,979, filed on Jun. 4, 2013.

(51) Int. Cl.
*A61C 19/00* (2006.01)
*A61C 1/08* (2006.01)
*A61C 3/02* (2006.01)

(52) U.S. Cl.
CPC *A61C 1/082* (2013.01); *A61C 3/02* (2013.01)

(58) Field of Classification Search
CPC ...... A61C 1/084; A61C 1/082; A61C 1/085; A61C 3/02
USPC .................................. 433/72–76; 606/80, 96
See application file for complete search history.

(56) References Cited

U.S. PATENT DOCUMENTS

| 4,144,645 | A  | 3/1979 | Marshall |
|-----------|----|--------|----------|
| D261,032  | S  | 9/1981 | Marucci et al. |
| D263,877  | S  | 4/1982 | Podszus et al. |
| D264,876  | S  | 6/1982 | Seid |
| D305,935  | S  | 2/1990 | Straihammer et al. |
| 5,545,039 | A  | 8/1996 | Mushabac |
| 5,725,376 | A  | 3/1998 | Poirier |
| 6,213,770 | B1 | 4/2001 | Kuhn |

(Continued)

FOREIGN PATENT DOCUMENTS

| DE | 4012327 | 10/1991 |
|----|---------|---------|
| DE | 4013828 | 1/1992  |

(Continued)

OTHER PUBLICATIONS

U.S. Appl. No. 29/447, 926, filed Mar. 7, 2013; Daniel Yonil Jung.

(Continued)

*Primary Examiner* — Heidi M Eide
(74) *Attorney, Agent, or Firm* — Thorpe, North & Western, LLP

(57) ABSTRACT

A dental cutting system and method for cutting a patient's tooth includes a hand piece to be held and carrying a cutting burr to cut the patient's tooth. A plurality of guide pins is attached to and extends from the hand piece of the cutting tool remote from the cutting bur. One or more cutting guides each have a cavity coinciding with at least a portion of teeth inside a patient's mouth that are adjacent to or remote from the patient's tooth to be cut. The guide pins of the handpiece slide in slots in the cutting guide to guide the cutting burr to cut the patient's tooth.

19 Claims, 25 Drawing Sheets

(56) References Cited

U.S. PATENT DOCUMENTS

| | | | |
|---|---|---|---|
| 6,443,731 B2 | 9/2002 | Kuhn et al. | |
| 6,511,323 B1 | 1/2003 | Wilkinson | |
| 6,702,578 B2 | 3/2004 | Matsutani et al. | |
| D499,486 S | 12/2004 | Kuhn et al. | |
| D548,342 S | 8/2007 | Cohen | |
| 7,346,417 B2* | 3/2008 | Luth | A61B 19/52 128/920 |
| 8,109,762 B2 | 2/2012 | Richard | |
| D708,330 S | 7/2014 | Jung | |
| 2005/0136374 A1 | 6/2005 | Carmichael et al. | |
| 2005/0234465 A1* | 10/2005 | McCombs et al. | 606/88 |
| 2007/0287127 A1 | 12/2007 | Schaffran et al. | |
| 2008/0139916 A1* | 6/2008 | Maier | A61B 19/52 600/407 |
| 2008/0287953 A1 | 11/2008 | Sers | |
| 2009/0011380 A1 | 1/2009 | Wang | |
| 2009/0298008 A1* | 12/2009 | Groscurth et al. | 433/74 |
| 2010/0112514 A1 | 5/2010 | Chen | |
| 2010/0112515 A1 | 5/2010 | Chen | |
| 2010/0192375 A1 | 8/2010 | Jacquemyns | |
| 2010/0196842 A1* | 8/2010 | Jacquemyns | 433/75 |
| 2010/0279243 A1* | 11/2010 | Cinader et al. | 433/3 |
| 2011/0091836 A1* | 4/2011 | Fujii | 433/75 |
| 2012/0270176 A1 | 10/2012 | Jacquemyns | |
| 2013/0017507 A1 | 1/2013 | Moffson et al. | |
| 2013/0123856 A1* | 5/2013 | Fritzinger et al. | 606/280 |
| 2014/0248577 A1* | 9/2014 | Tahmasebi et al. | 433/75 |

FOREIGN PATENT DOCUMENTS

| | | |
|---|---|---|
| WO | WO 2009/000505 A1 | 12/2008 |
| WO | WO 2011/091382 A1 | 7/2011 |
| WO | WO 2012/110850 | 8/2012 |
| WO | WO 2012/162605 | 11/2012 |

OTHER PUBLICATIONS

U.S. Appl. No. 29/453, 863, filed May 3, 2013; Daniel Yonil Jung.
PCT Application PCT/US14/19048; Digitalprep Technologies, Inc.; international search report mailed May 22, 2014.

* cited by examiner

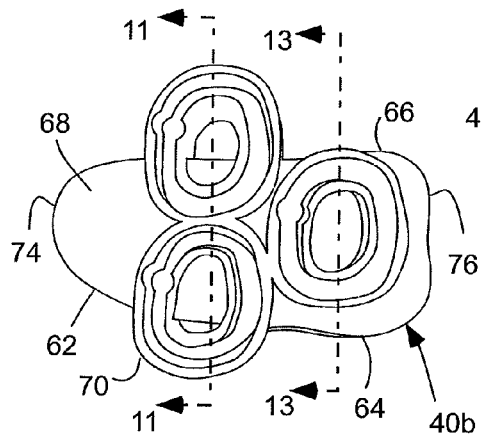 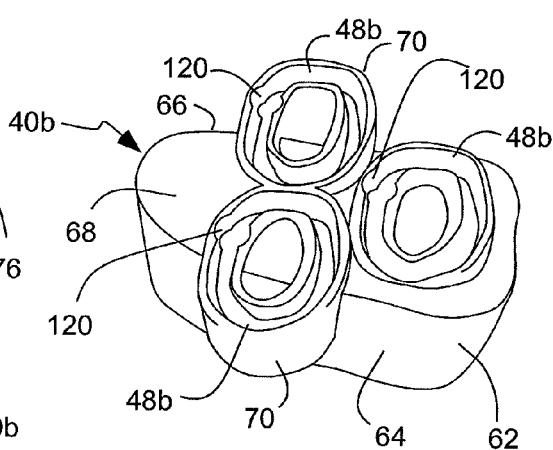
Fig. 9          Fig. 10
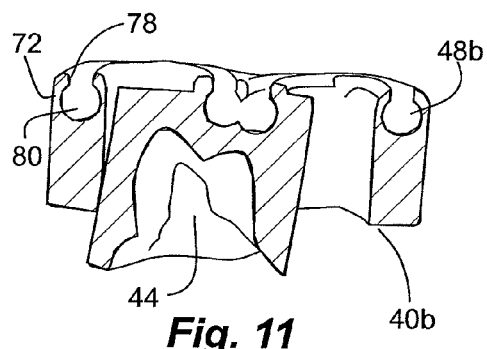 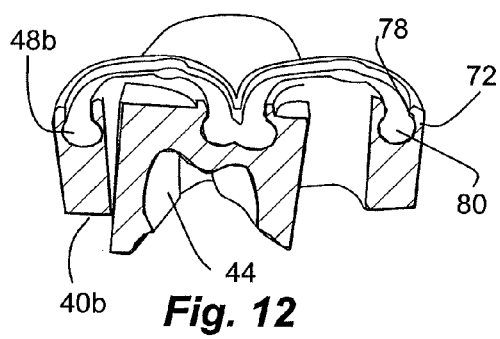
Fig. 11          Fig. 12
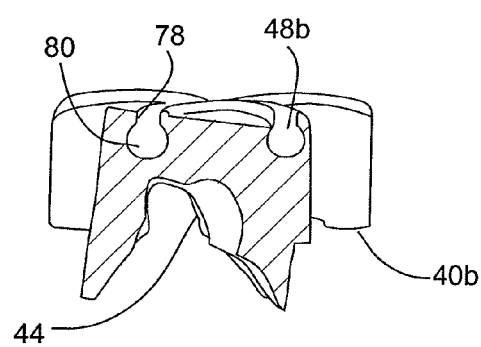
Fig. 13

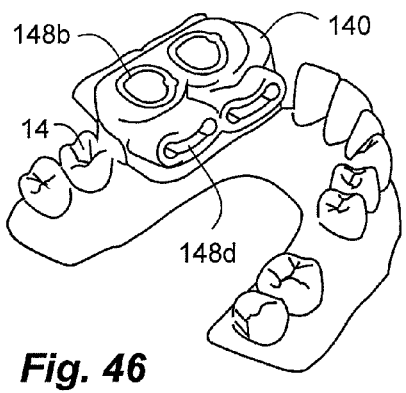
Fig. 46
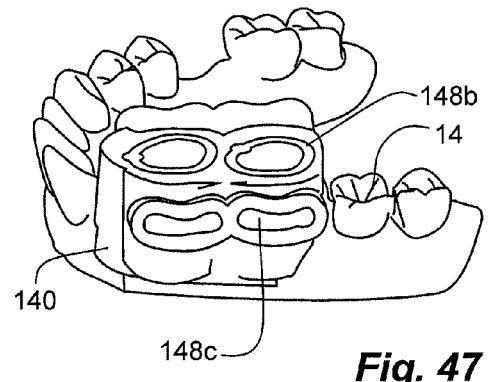
Fig. 47
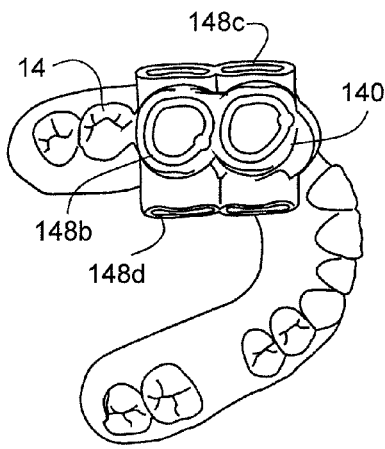
Fig. 48
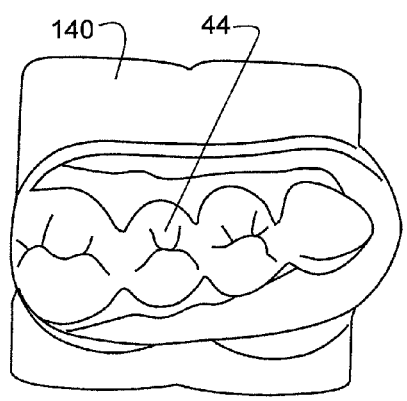
Fig. 49
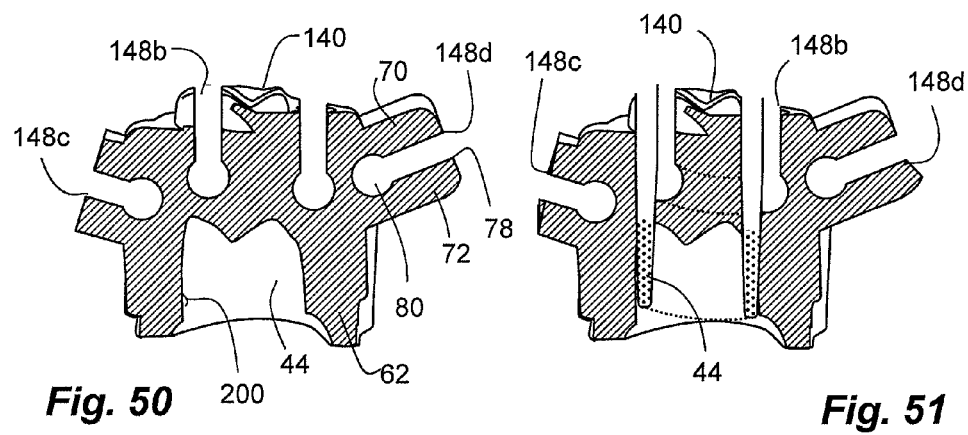
Fig. 50
Fig. 51

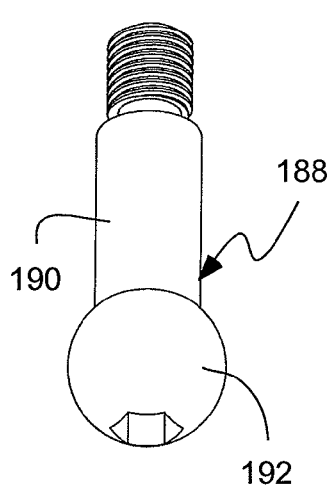
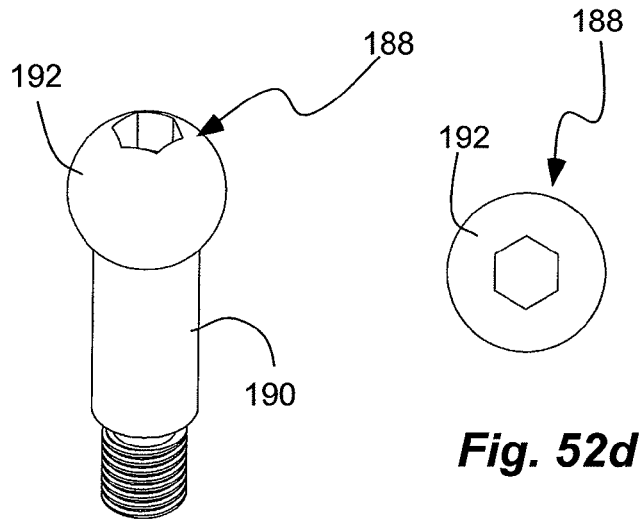
*Fig. 52b*     *Fig. 52c*     *Fig. 52d*
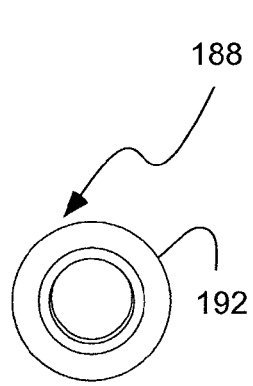
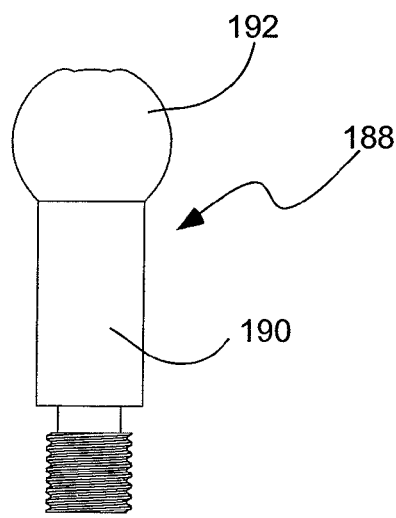
*Fig. 52e*
*Fig. 52a*

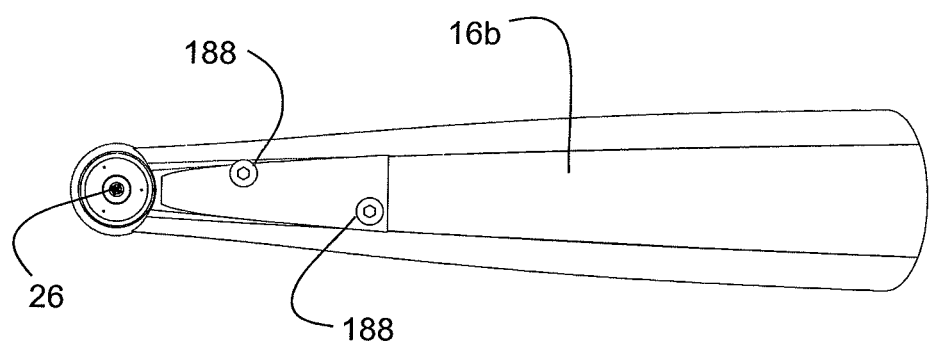
*Fig. 56*
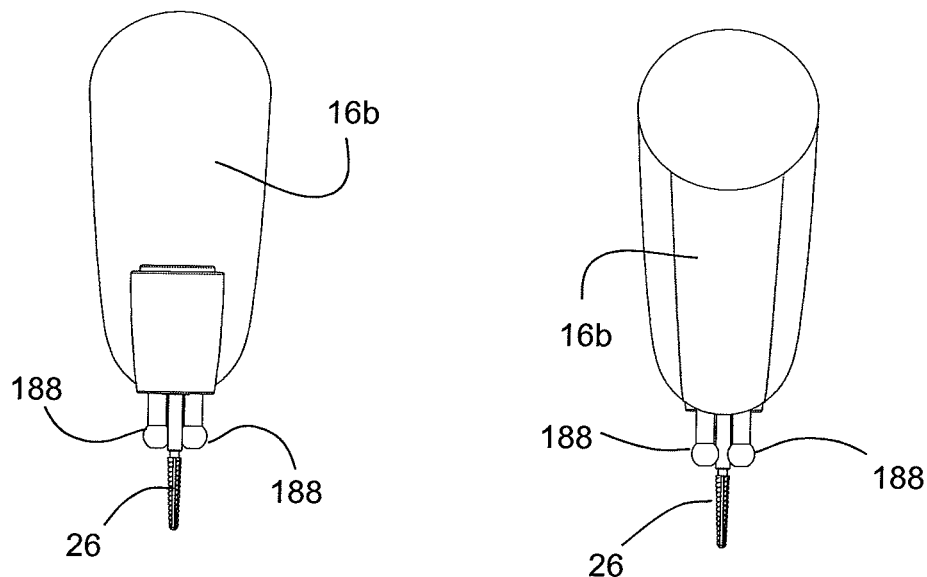
*Fig. 57*  *Fig. 58*

DENTAL CUTTING SYSTEM AND METHOD WITH REMOTE CUTTING GUIDE

PRIORITY CLAIM & RELATED APPLICATIONS

This application claims the benefit of U.S. Provisional Application Ser. No. 61/770,248, filed Feb. 27, 2013; and 61/830,979, filed Jun. 4, 2013; which are hereby incorporated herein by reference.

This is related to U.S. patent application Ser. No. 14/158,558, filed Jan. 17, 2014, which claims priority to U.S. Provisional Patent Application Ser. Nos. 61/754,894, filed, Jan. 21, 2013; which are hereby incorporated herein by reference.

This is related to U.S. Design patent application Ser. No. 29/447,933, filed Mar. 7, 2013; and 29/453,863, filed May 3, 2013; which are hereby incorporated herein by reference.

This is related to U.S. patent application Ser. No. 14/186,515, filed Feb. 21, 2014, which claims priority to U.S. Provisional Patent Application Ser. Nos. 61/767,704 and 61/767,749, filed, Feb. 21, 2013; which are hereby incorporated herein by reference.

BACKGROUND

1. Field of the Invention

The present invention relates generally to a dental cutting system with a remote cutting guide remote from the working tooth and guide pins remote from the cutting tool or burr.

2. Related Art

Various methods have been proposed to cut a patient's tooth. Some methods prepare a user's tooth or adjacent teeth to receive a crown. Some methods provide a cutting guide or template. For example, see U.S. Pat. Nos. 5,725,376 and 4,144,645; US Patent Publication Nos. 2010/0196842; 2010/0192375 and 2012/0270176; PCT Publication No. WO2012/110850; and German Patent Nos. DE 4012327 and DE 4013828. One issue with cutting guides is that the cutting tool can inadvertently cut the guide or template, resulting in an inaccurate guide or template, and inadvertent cutting of the patient's tooth, such as a nerve inside the tooth. In addition, some cutting guides can overly restrict the cutting tool. Furthermore, some cutting systems require custom cutting tools, or cutting tools with non-standard sizes and shapes.

SUMMARY OF THE INVENTION

It has been recognized that it would be advantageous to develop a system and method to cut a patient's tooth to receive a prosthesis or restoration and to resist inadvertent cutting of the guide or template, and thus resist medical injury. In addition, it has been recognized that it would be advantageous to develop a system and method to cut a patient's tooth with a guide or template that allows the dentist to view the tooth being cut during cutting. In addition, it has been recognized that it would be advantageous to develop a system and method to cut a patient's tooth with increases stability and in a secure manner. Furthermore, it has been recognized that it would be advantageous to develop a system and method to cut a patient's tooth that resists contact between a cutting burr and the cutting guide, to thus resist injury or inadvertent cutting. The invention provides a dental cutting system for cutting a patient's tooth. The system comprises at least one cutting guide having at least one cavity to match at least a portion of at least one of a patient's teeth inside a patient's mouth adjacent to or remote from the patient's tooth to be cut. A plurality of slots in the cutting guide extends from an exterior of the cutting guide into the cutting guide. Each of the plurality of slots has a cross-sectional shape, transverse to a longitudinal length of the slot, with a narrower exterior and an enlarged interior. A handpiece is configured to be held and carries a cutting tool with a cutting burr configured to cut the patient's tooth. A plurality of guide pins is attached to and extends from the handpiece, and is located laterally and/or longitudinally remote from the cutting bur with respect to the handpiece. Each of the plurality of guide pins has a narrower neck and an enlarged head. The plurality of guide pins is slidable in the plurality of slots to guide the cutting burr with respect to the patient's tooth to be cut.

In accordance with a more detailed aspect of the invention, the at least one cutting guide can be placed on the least one of the patient's teeth with the cavity of the cutting guide matching at least a portion of at least one of the patient's teeth while leaving the patient's tooth to be cut exposed; the enlarged head of each of the plurality of guide pins can be inserted into a different one of the plurality of slots in the at least one cutting guide; and the plurality of guide pins can be displaced along the plurality of slots to guide the cutting burr and displace the cutting burr with respect to the tooth to be cut In addition, the invention provides dental cutting system for cutting a patient's tooth, comprising a plurality of cutting guides each having at least one cavity therein coinciding with at least a portion of teeth inside a patient's mouth that are adjacent to or remote from the patient's tooth to be cut to expose the patient's tooth to be cut with respect to the cutting guide. Each of the plurality of cutting guides comprises a plurality of slots in the cutting guide extending from an exterior of the cutting guide into the cutting guide. Each of the plurality of slots has a cross-sectional shape, transverse to a longitudinal length of the slot, with a narrower exterior and an enlarged interior. The plurality of cutting guides comprises: 1) an occlusal cutting guide with occlusal slots located laterally on the occlusal cutting guide; and 2) a buccal or a lingual or both cutting guide with buccal or lingual or both slots located on an occlusal wall of the cutting guide. A handpiece has a handle configured to be held and a head with a cutting tool with a cutting burr configured to cut the patient's tooth. A plurality of guide pins is attached to and extends from the handle of the handpiece and is located remote from the cutting burr and the head. Each of the plurality of guide pins has a narrower neck and an enlarged head. The plurality of guide pins is slidable in the at least one slot to guide the cutting burr with respect to the patient's tooth to be cut.

In addition, the invention provides a cutting tool device for cutting a patient's tooth, comprising a hand piece with a handle configured to be held and having a head with a cutting burr configured to cut the patient's tooth. A plurality of guide pins is attached to and extends from the handle of the handpiece at a location remote from the cutting bur and the head.

Furthermore, the invention provides a method for cutting a patient's tooth, comprising: placing a cutting guide on at least one of the patient's teeth with a cavity of the cutting guide matching at least a portion of at least one of the patient's teeth at a location remote from the patient's tooth to be cut and leaving the patient's tooth to be cut exposed with respect to the cutting guide; inserting an enlarged head of each of a plurality of guide pins into a different one of a plurality of slots in the at least one cutting guide, the plurality of guide pins being attached to and extending from the handpiece and located remote from a cutting burr; and displacing the guide pins along the plurality of slots to guide the cutting burr with respect to the patient's tooth to be cut.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 9 is a top view of the dental guide of the dental cutting system of FIG. 1;

FIG. 10 is a perspective view of the dental guide of the dental cutting system of FIG. 1;

FIG. 11 is a cross-sectional end view of the dental guide of the dental cutting system of FIG. 1, taken along line 11 of FIG. 9;

FIG. 12 is a cross-sectional perspective view of the dental guide of the dental cutting system of FIG. 1, taken along line 11 of FIG. 9;

FIG. 13 is a cross-section end view of the dental guide of the dental cutting system of FIG. 1, taken along line 13 of FIG. 9;

FIGS. 30b and 30c are perspective view of the guide pin of FIG. 30a;

FIG. 30d is a top view of the guide pin of FIG. 30a;

FIG. 30e is a bottom view of the guide pin of FIG. 30a;

FIG. 46 is a perspective view of the cutting guide of the dental cutting system of FIG. 37;

FIG. 47 is a perspective view of the cutting guide of the dental cutting system of FIG. 37;

FIG. 48 is a top view of the cutting guide of the dental cutting system of FIG. 37;

FIG. 49 is a bottom view of the cutting guide of the dental cutting system of FIG. 37;

FIG. 50 is a cross-sectional schematic view of the cutting guide of the dental cutting system of FIG. 37;

FIG. 51 is a cross-sectional schematic view of the cutting guide of the dental cutting system of FIG. 37, shown with the cutting burr;

FIG. 52*a* is a side view of a guide pin of the handpiece of the dental cutting system of FIG. 37;

FIGS. 52*b* and 52*c* are perspective view of the guide pin of FIG. 52*a;*

FIG. 52*d* is a top view of the guide pin of FIG. 52*a;*

FIG. 52*e* is a bottom view of the guide pin of FIG. 52*a;*

FIG. 56 is a bottom view of the handpiece of FIG. 53;

FIG. 57 is an end view of the handpiece of FIG. 53;

FIG. 58 is an end view of the handpiece of FIG. 53;

The patient's teeth in the above drawings are shown by way of example with respect to the patient's lower teeth with the understanding that the cutting system of the present invention can be used on the patient's upper teeth as well. Similarly, terms of reference, such as top and bottom, are used with respect to the bottom teeth with the understanding that such terms of reference are relative to the patient's teeth, and inverted with respect to the upper teeth.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The terms "buccal" and "lingual" are used herein to refer to an outside and a inside, respectively, face or side of a tooth with respect to the user's mouth, and are generally opposite one another, with "buccal" referring to an outside of the tooth generally facing the patient's check or lips, and "lingual" referring to an inside of the tooth generally facing the user's tongue. The terms buccal and lingual are also used herein to refer to directions and locations with respect to the tooth.

The terms "mesial" and "distal" are used herein to refer to a proximal side and a distal side, respectively of the tooth with respect to the user's mouth, and are generally opposite one another, with mesial referring to a front of the user's mouth and distal referring to a back of the user's mouth along a row of teeth.

The term "occlusal" is used herein to refer to a top face of a tooth that faces an opposing tooth when the patient's jaw is closed, and extends between the sides (buccal, lingual, mesial and distal) of the tooth. While the term occlusal generally refers to the posterior teeth, it is used interchangeably with the term "incisal" which generally refers to the anterior teeth.

The term "cutting tool" is used herein to refer to a tool that cuts, and has a cutting surface, such as a bur, and a shank that extends from the cutting surface to be held by a chuck or motor. The cutting surface or burr can have cutting or grinding surfaces or materials. The chuck and/or motor can be part of a dental handpiece that is held by the dentist.

Description

Figure 1:
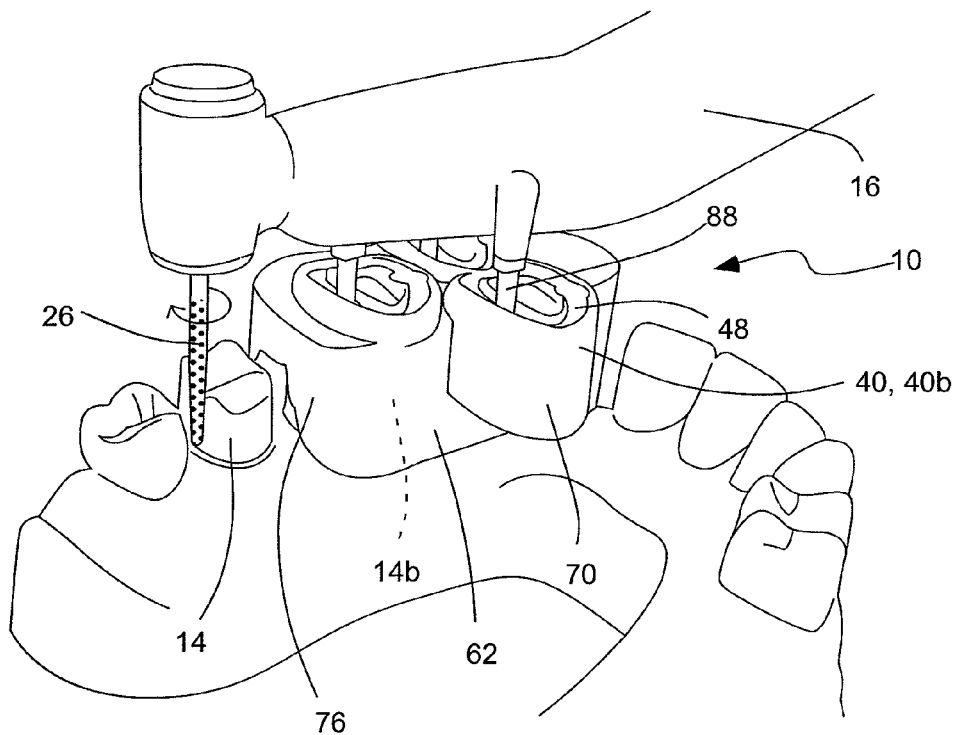
FIG. 1 is a perspective view of a dental cutting system in accordance with an embodiment of the present invention shown with a handpiece with a cutting burr and a plurality of guide pins slidable in a plurality of slots of a dental guide (buccal, lingual, mesial and distal) for cutting a patient's tooth.
Figure 68:
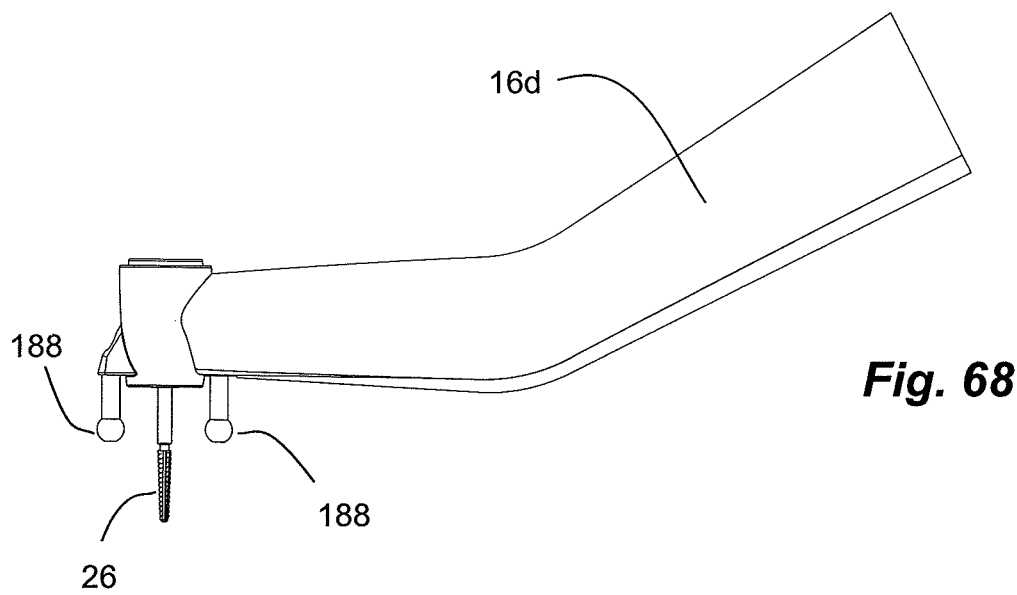
FIG. 68 is a side view of the handpiece of FIG. 66.

As illustrated in FIGS. 1-68, a dental cutting system and method are shown in an example implementation in accordance with the invention for cutting a patient's tooth. For example, one or more teeth can be cut to receive a dental prosthesis or restoration, such as a crown, bridge, veneer, inlay, etc. The system and method can include one or more cutting guides, templates, guides, guide bodies, overlays or the like that have at least one cavity to match at least a portion of at least one of the patient's teeth inside a patient's mouth that are adjacent to, and/or remote from, the patient's tooth to be cut. For example, the cutting guide can have a cavity that includes cavities to match a series of teeth, or at least a portion thereof, such as the adjacent tooth, or teeth adjacent an intermediate tooth or the tooth to be cut (or working tooth). The cutting guide can include one or more slots extending from an exterior of the cutting guide into the cutting guide. The slots can be sized, positioned and oriented to receive and guide corresponding guide pins on handpiece that carries a cutting tool; and to allow the guide pins to be moved through the slots in a predetermined cutting pattern, including depth, position and orientation, to guide the handpiece, and thus the cutting tool, to cut a predetermined pattern in the patient's tooth or teeth. Thus, the slots in the cutting guide can guide the guide pins, and thus the cutting tool along a path of travel. The cut in the patient's tooth can receive a dental prosthesis (such as a crown, bridge, veneer, inlay, etc.). The slots can have a cross-sectional shape (transverse to a longitudinal length of the slot) with a narrower exterior and an enlarged interior, such as key-shaped. The cutting guide can be made from plastic, and can be formed by 3D printing, milling, etc. The cutting guide, including the slots and cavity(ies), can be custom made based on a 3D scan of the patient's teeth, and model of the dental prosthesis. Thus, the cutting guide can be placed on the patient's teeth, with the cavities matching and mating, and holding the slots with respect to the teeth, so that the cutting tool cuts the tooth to receive the preformed prosthesis or restoration. In practice, a dentist can scan the patent's teeth in a first visit, or take an impression of the patent's teeth which can be scanned, or from which a model can be made that can be scanned, in a first visit. The scan can be used to create a digitized model of the patient's teeth. The cut(s) to the tooth can be modeled or generated based on the digitized model of the patient's teeth. The cutting tool making the cut(s) can also be modeled. The dental guide(s) can be modeled based on the patent's teeth and the cut(s), and the cutting tool. The dental guide(s) can be formed, such as by 3D printing or milling. The dental prosthesis or restoration can be modeled from the model of the cut tooth and the patient's teeth. The dental prosthesis or restoration can be formed, such as by milling.

As described above, it is possible in some previous systems for the burr of the cutting tool to inadvertently cut the cutting guide, such as being inadvertently inserted into the slot while rotating, thus cutting the slot or guide defining the slot. Such an inadvertent cut in the cutting guide can result in an inaccurate guide or template, and inadvertent cutting of the patient's tooth, such as a nerve inside the tooth. Alternatively, it is possible in some previous systems for the shank of the cutting tool to bear against the wall of the cutting guide at high revolutions per minute, and thus grind away the wall, or create friction that could heat and melt the wall. Cutting or deforming the wall of the cutting guide or slot can cause a deviation of the cutting tool so that the dental prosthetic does not fit or match, or cutting too deep and hurt the patient. Furthermore, some previous systems cover the tooth to be cut with the cutting guide, preventing or impeding the dentist's ability to see the tooth being cut.

The system and method of the invention includes the cutting guide adjacent to or remote from the patient's tooth to be cut so that the cutting guide does not cover the tooth to be cut, or inhibit the dentist's ability to see the tooth to be cut. In addition, the slots are laterally and/or longitudinally remote from the tooth to be cut (or remote in the buccal and/or lingual direction, or remote in the mesial and/or distal direction). Furthermore, the guide pins are attached to and extend from the handpiece at a location laterally and/or longitudinally remote from the cutting bur. The guide pins are slidable in the slots to guide the cutting burr with respect to the patient's tooth to be cut. The slots can have a cross-sectional shape (transverse to a longitudinal length of the slot) with a narrower exterior or opening and an enlarged interior or cavity, while the guide pins can have a narrower neck and an enlarged head. The guide pins can have a cross-sectional shape that matches a cross-sectional shape of the slots, or an outer profile that matches or mates with the inner profile of the slots. For example, the guide pins can have an enlarge head or orb with a round or circular shape on a narrower neck or shank or shaft. The guide pins can slide in the slots as the cutting tool and burr rotate to cut the tooth. The guide pins are retained in the slots by the enlarged heads or orbs of the guide pints, and the narrower exterior or opening in the slots.

Referring to FIGS. 1-36, the dental cutting system 10 for cutting a patient's tooth 14 can comprise at least one cutting guide, with at least one slot therein, and a dental handpiece 16 with a cutting tool 18 that is guided by the slot. The dental handpiece is configured to be held by a dentist, and can have a shank with a grip or handle on a proximal end that can be grasped and used to manipulate the handpiece, and thus the cutting tool. The handpiece can have a head on a distal end that carries the cutting tool, such as with a chuck on a distal end thereof. The head can have a driver, such as a motor or turbine, to turn the chuck and the cutting tool. The cutting tool 18 can have a shank 22 and a cutting burr 26 configured to cut the patient's tooth 14. The shank 22 can be received by the chuck of the dental handpiece 16. The cutting tool 18, or shank 22 and cutting burr 26, can extend transverse to a longitudinal axis of the handpiece. In one aspect, the cutting burr can have cutting edges or surfaces. In another aspect, the cutting burr of the cutting tool can have an abrasive or grinding cutting surface. In one aspect, standard cutting tools, with standard shapes and sizes, can be used. Thus, the dentist can utilized tools already acquired without having to obtain custom and costly non-standard cutting tools. In addition, the standard cutting tools can be modeled in order to model the cuts to the tooth and to model the cutting guide. Similarly, the handpiece and guide pins can be modeled.

Figure 17:
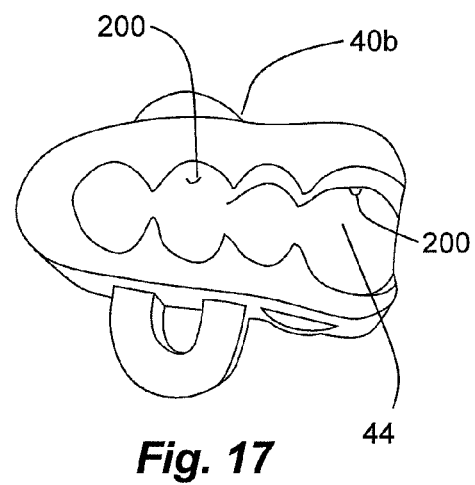
FIG. 17 is a bottom view of the dental guide of the dental cutting system of FIG. 1.
Figure 18:
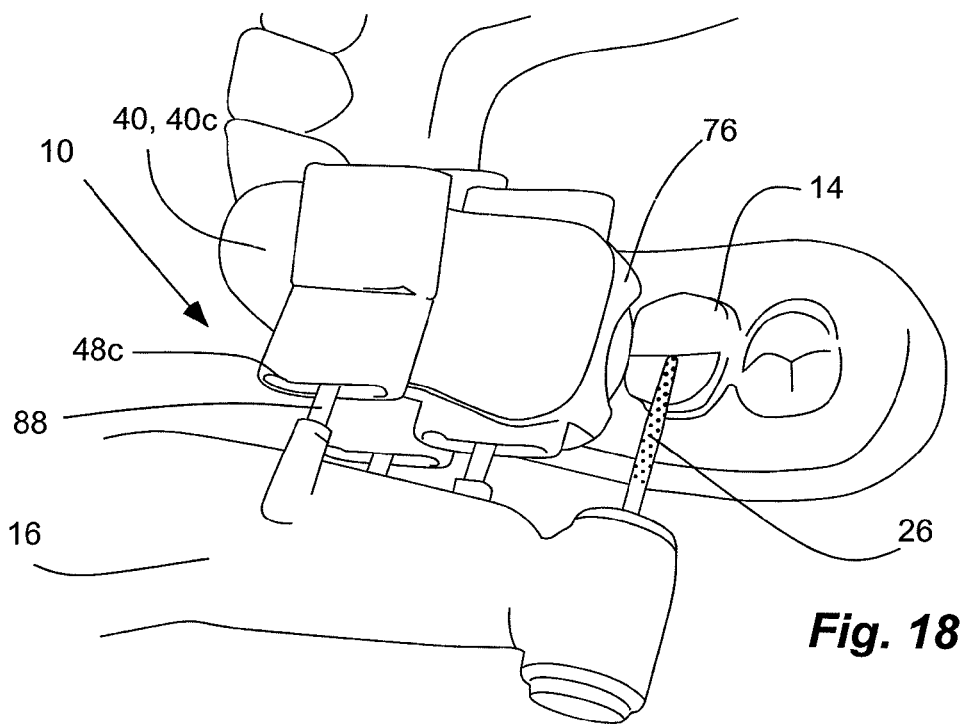
FIG. 18 is a perspective view of the dental cutting system in accordance with the embodiment of the present invention of FIG. 1, further showing a dental guide (occlusal) for cutting a patient's tooth.
Figure 19:
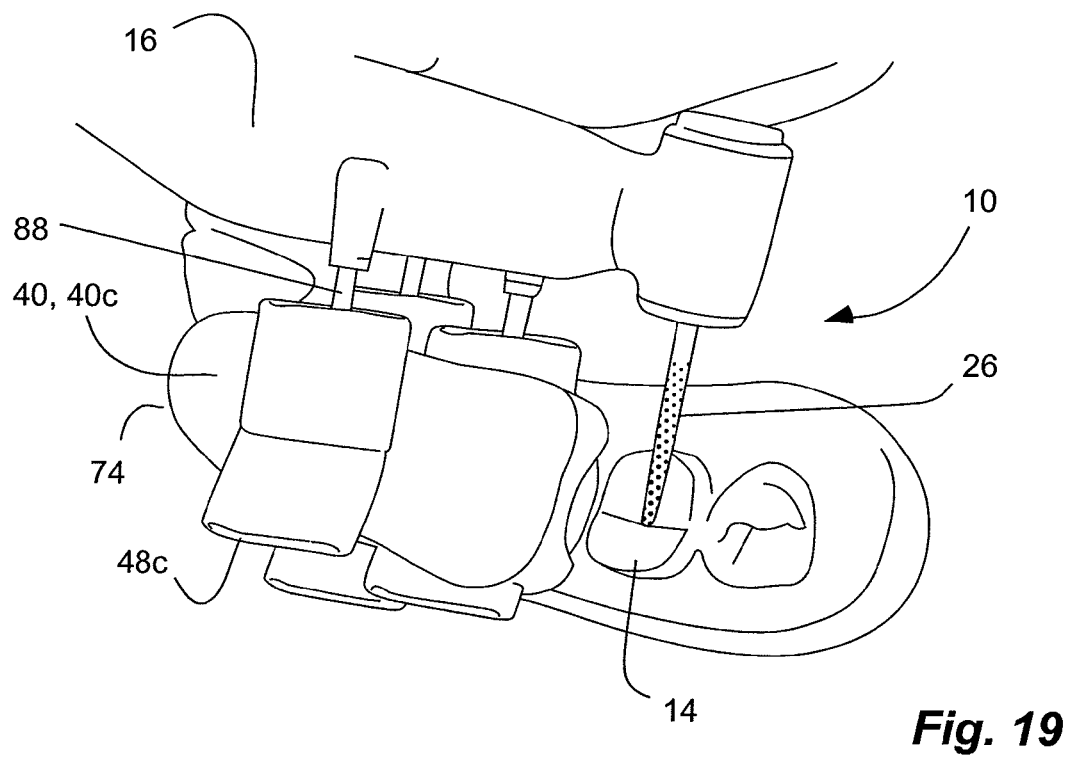
FIG. 19 is a perspective view of the dental cutting system of FIG. 18.
Figure 20:
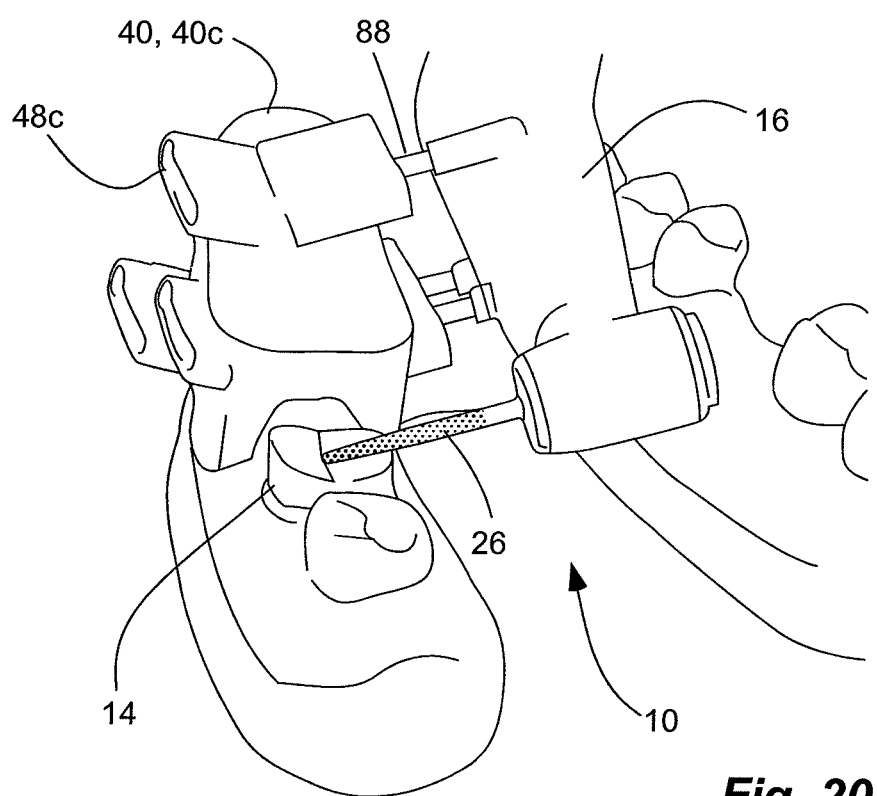
FIG. 20 is a perspective view of the dental cutting system of FIG. 18.
Figure 21:
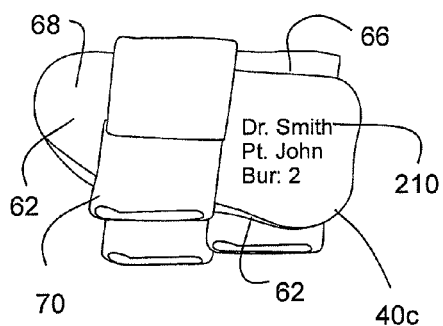
FIG. 21 is a top view of the dental guide of the dental cutting system of FIG. 18.
Figure 22:
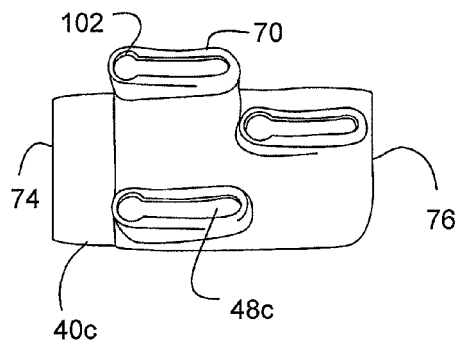
FIG. 22 is a side view of the dental guide of the dental cutting system of FIG. 18.
Figure 23:
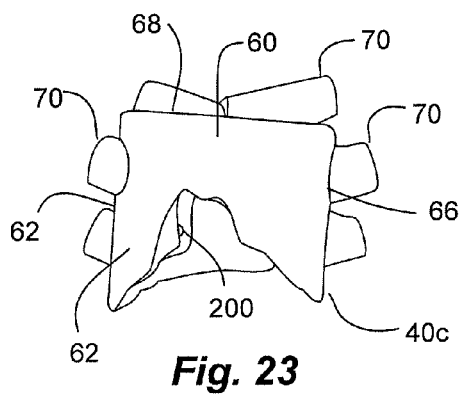
FIG. 23 is an end view of the dental guide of the dental cutting system of FIG. 18.
Figure 24:
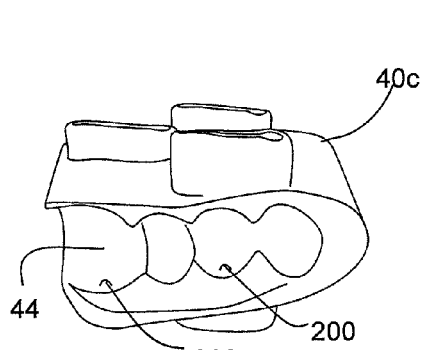
FIG. 24 is a bottom perspective view of the dental guide of the dental cutting system of FIG. 18.
Figure 25:
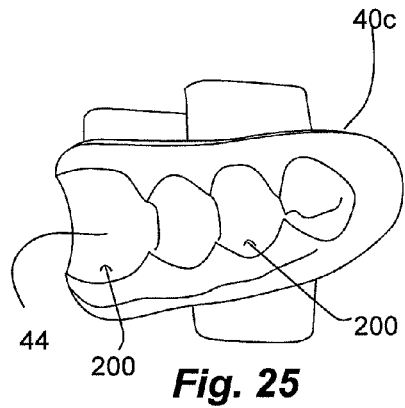
FIG. 25 is a bottom view of the dental guide of the dental cutting system of FIG. 18.
Figure 26:
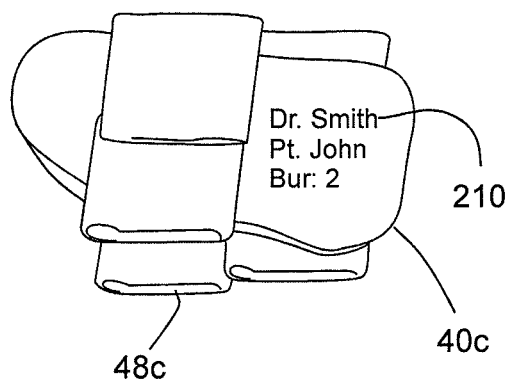
FIG. 26 is a top view of the dental guide of the dental cutting system of FIG. 18.
Figure 27:
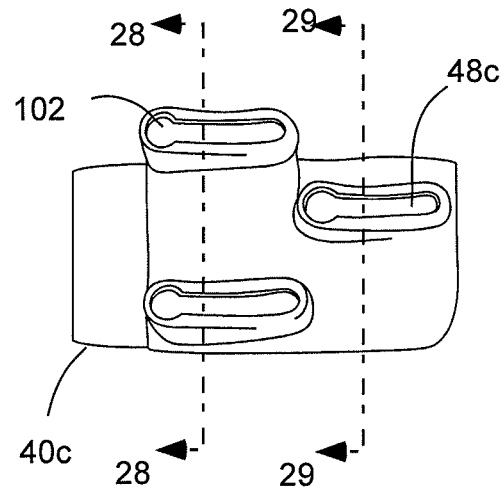
FIG. 27 is a side view of the dental guide of the dental cutting system of FIG. 18.
Figure 28:
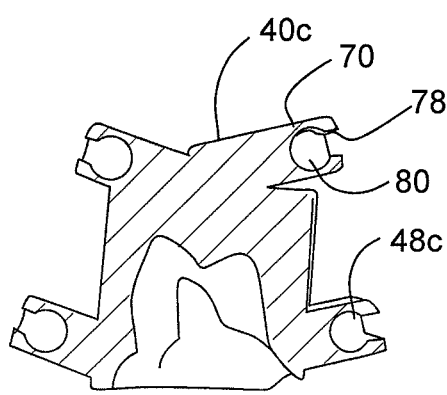
FIG. 28 is a cross-sectional end view of the dental guide of the dental cutting system of FIG. 18, taken along line 28 of FIG. 27.
Figure 29:
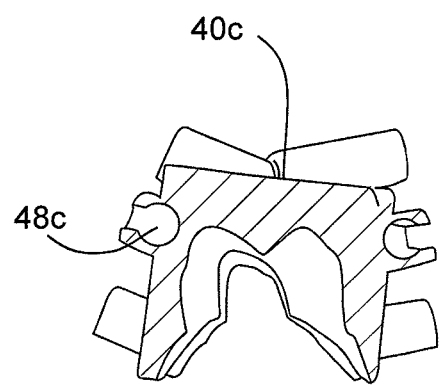
FIG. 29 is a cross-sectional end view of the dental guide of the dental cutting system of FIG. 18, taken along line 29 of FIG. 27.
Figure 30B:
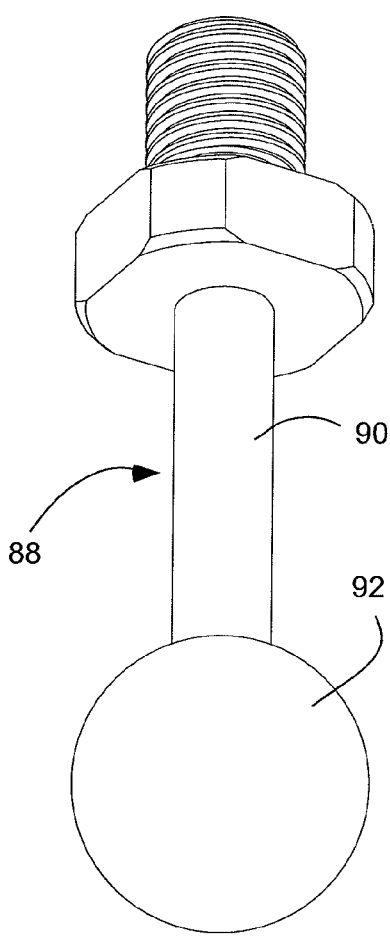
Figure 30C:
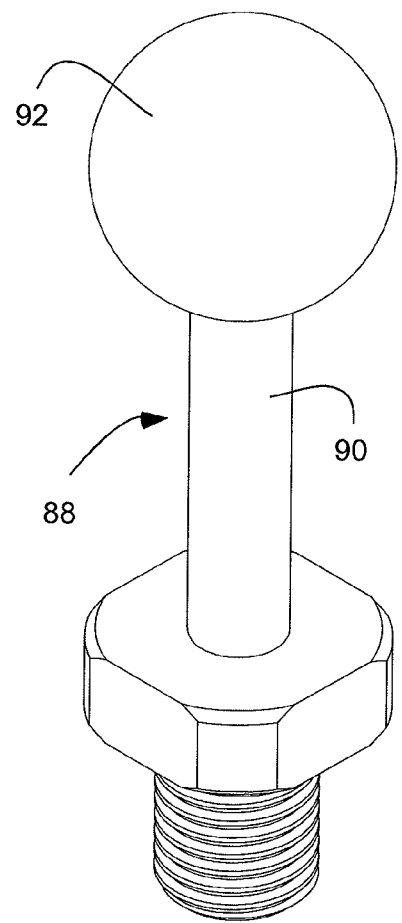
Figure 30D:
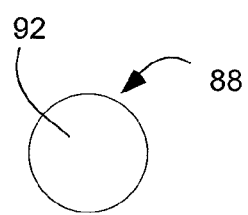
Figure 30A:
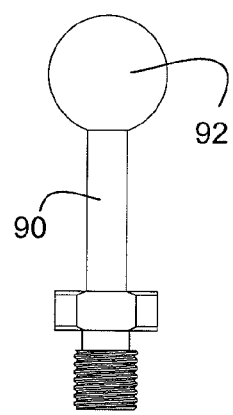
FIG. 30a is a side view of a guide pin of the handpiece of the dental cutting system of FIGS. 1 (and 18)
Figure 30E:
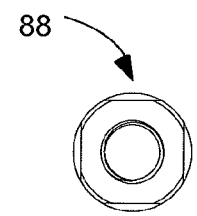
Figure 31:
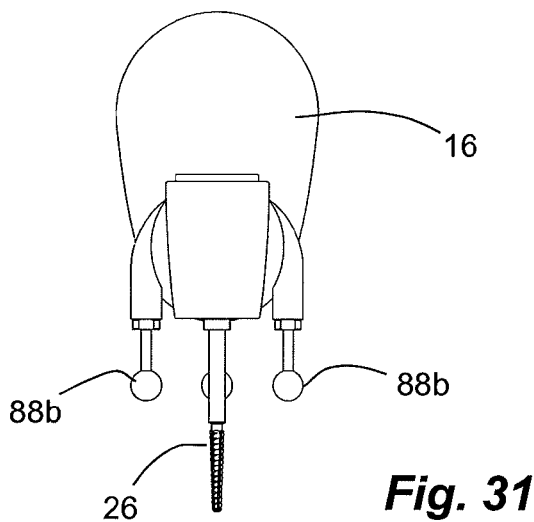
FIG. 31 is an end view of the handpiece of the dental cutting system of FIGS. 1 (and 18)
Figure 37:
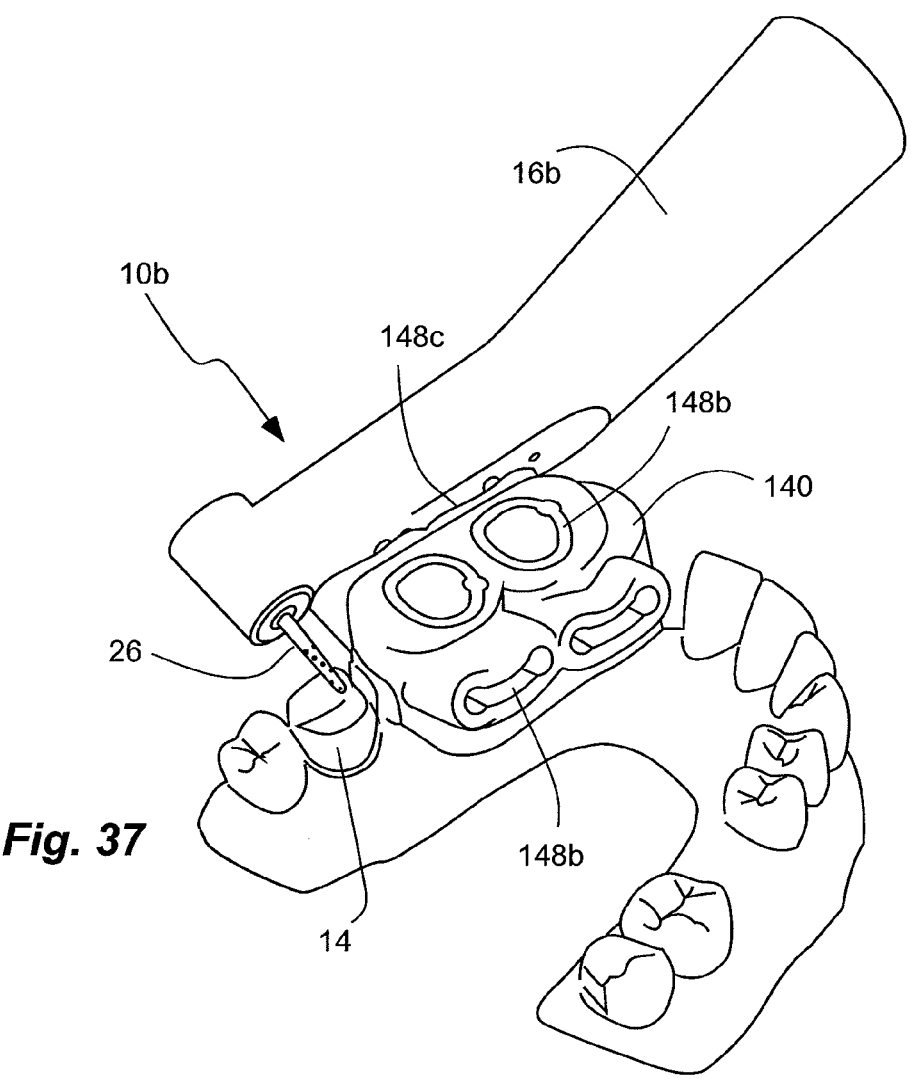
FIG. 37 is a perspective view of another dental cutting system in accordance with another embodiment of the present invention shown with another handpiece with a cutting burr and a plurality of guide pins slidable in a plurality of slots of a dental guide (buccal, lingual, mesial and distal; and occlusal) for cutting a patient's tooth.
Figure 38:
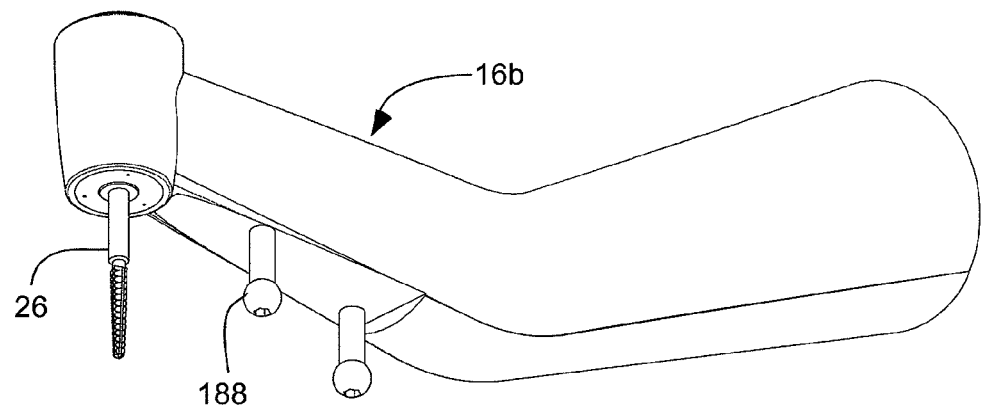
FIG. 38 is a perspective view of the handpiece of the dental cutting system of FIG. 37.
Figures 39, 40:
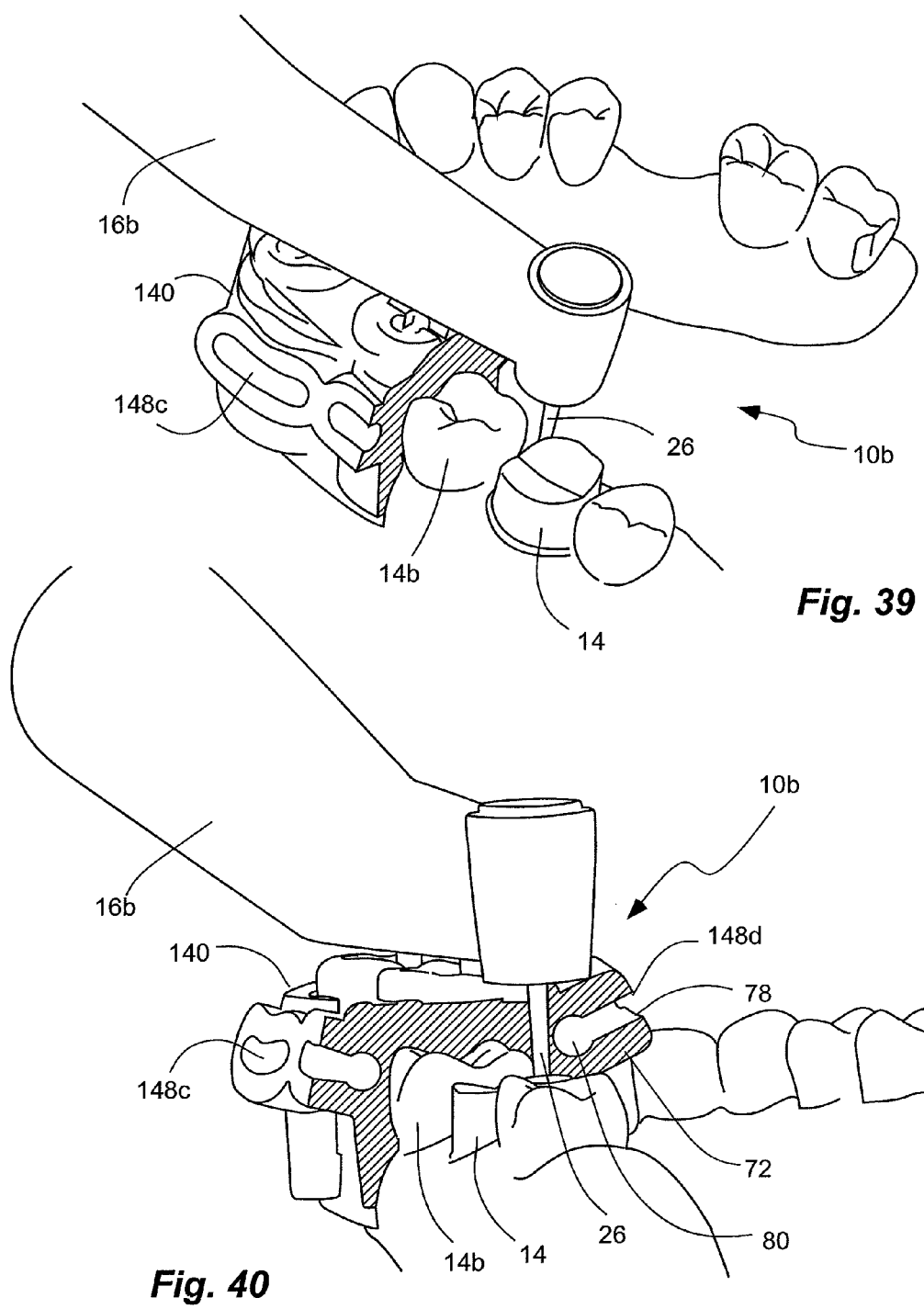
FIG. 39 is a partial perspective view of the dental cutting system of FIG. 37, shown with the cutting guide in cross-section.
FIG. 40 is a partial perspective view of the dental cutting system of FIG. 37, shown with the cutting guide in cross-section.
Figure 41:
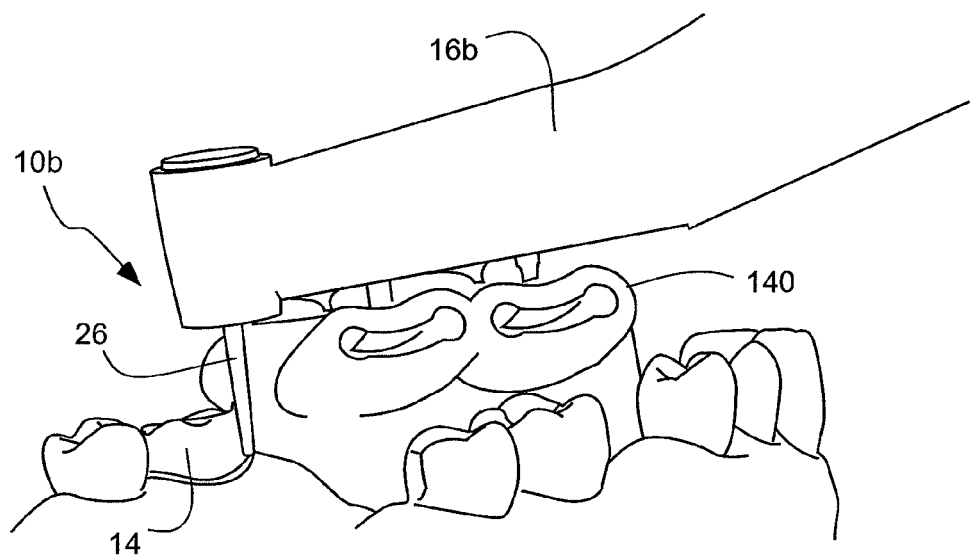
FIG. 41 is a perspective view of the dental cutting system of FIG. 37.
Figure 42:
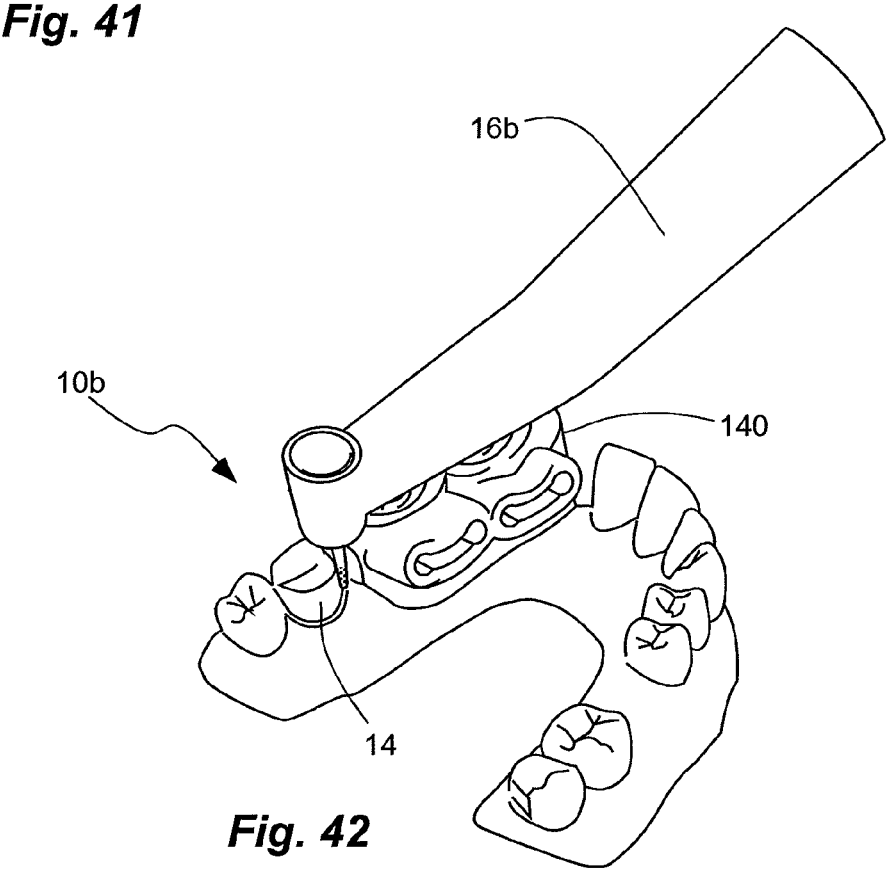
FIG. 42 is a perspective view of the dental cutting system of FIG. 37.
Figure 43:
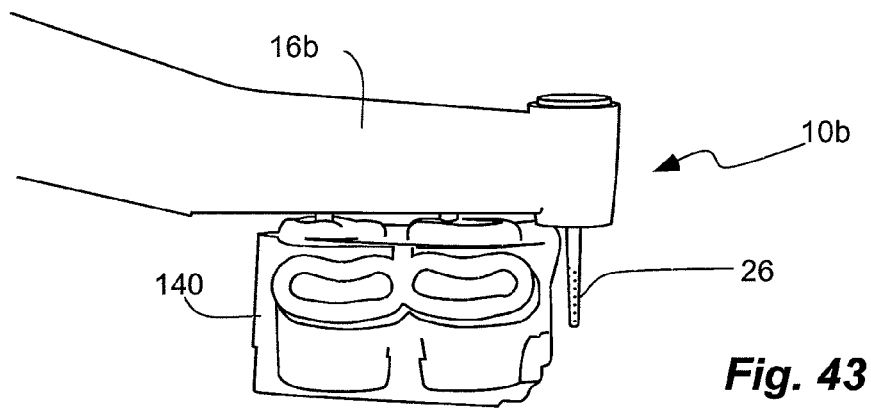
FIG. 43 is a side view of the dental cutting system of FIG. 37, shown without the patient's teeth.
Figure 44:
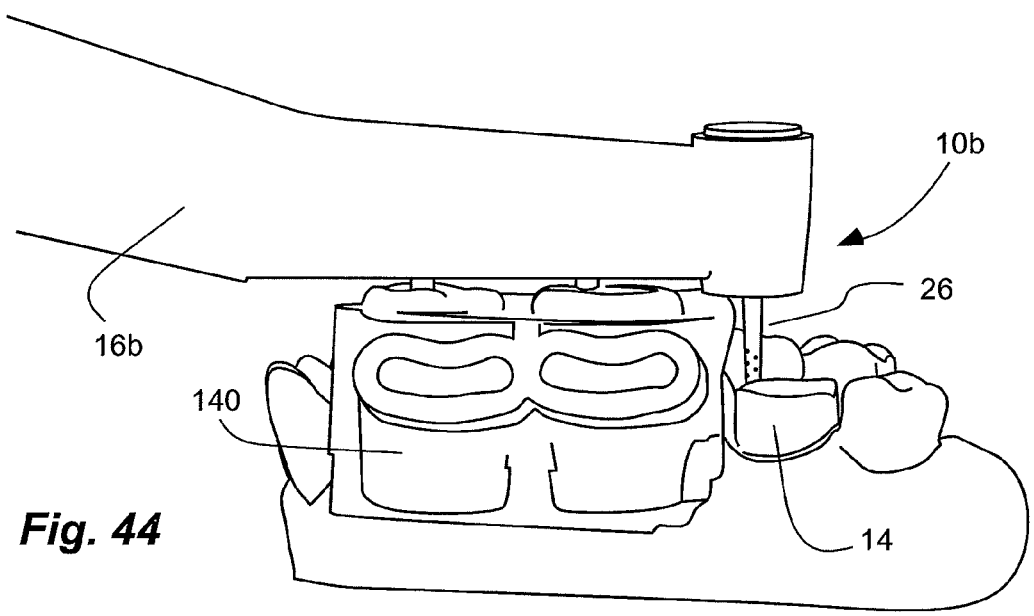
FIG. 44 is a side view of the dental cutting system of FIG. 37.
Figure 45:
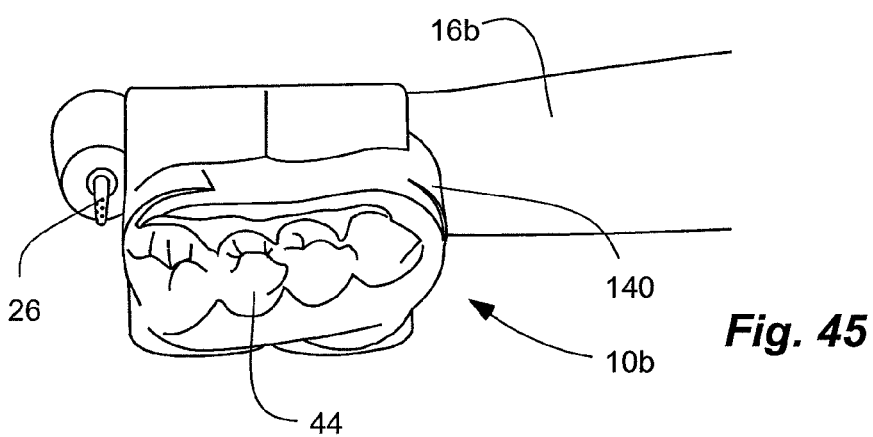
FIG. 45 is a bottom view of the dental cutting system of FIG. 37, shown with the patient's teeth removed.
Figure 53:
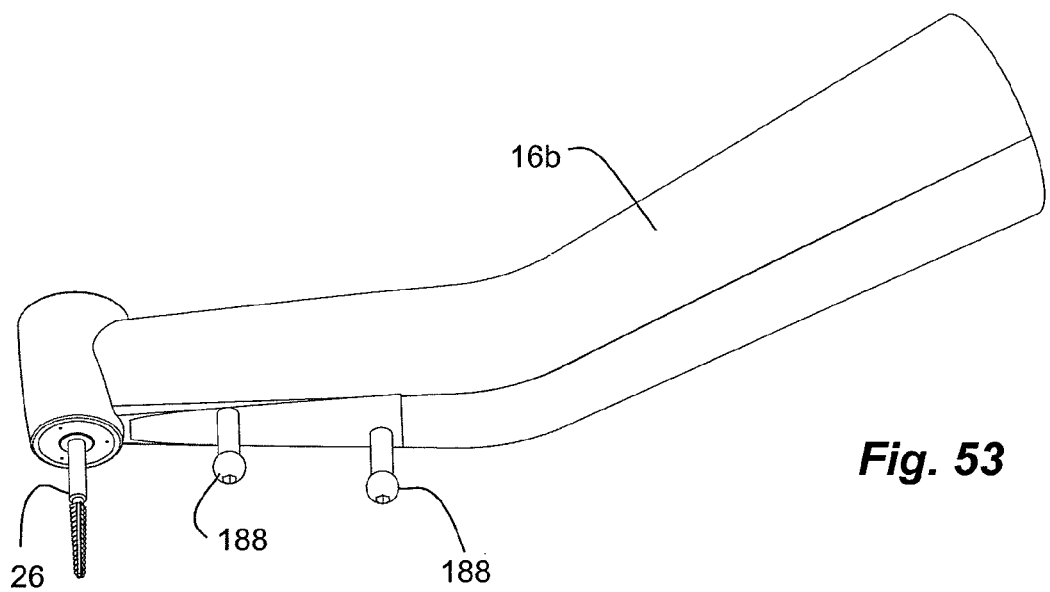
FIG. 53 is a perspective view of the handpiece of the dental cutting system of FIG. 37.
Figure 54:
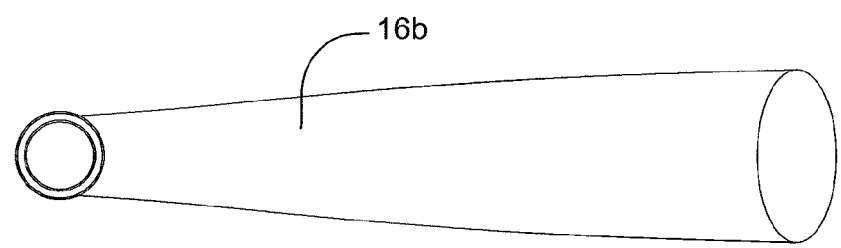
FIG. 54 is a top view of the handpiece of FIG. 53.
Figure 55:
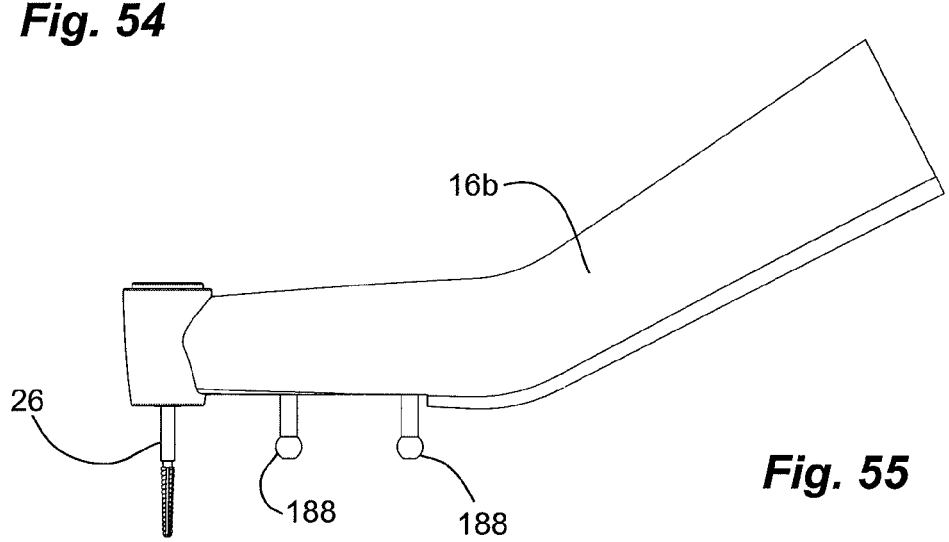
FIG. 55 is a side view of the handpiece of FIG. 53.
Figure 59:
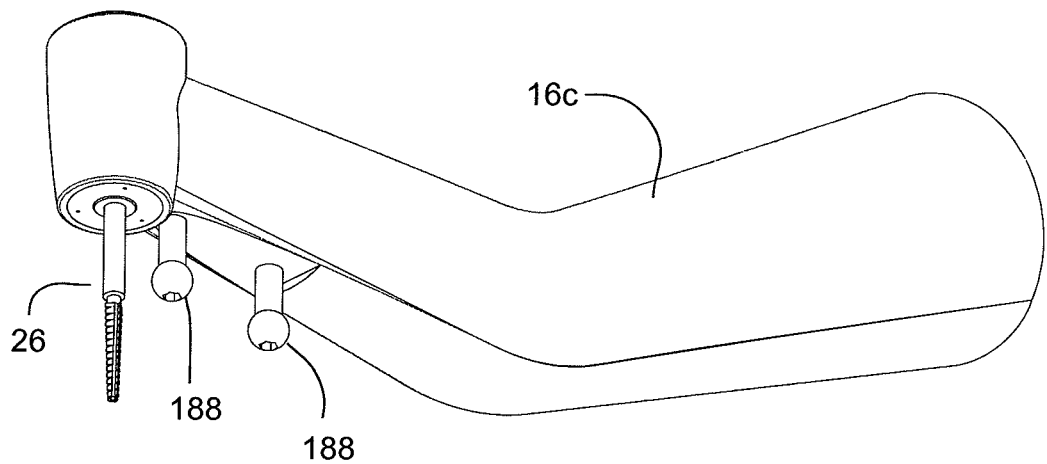
FIG. 59 is a perspective view of another handpiece in accordance with another embodiment of the present invention.
Figure 60:
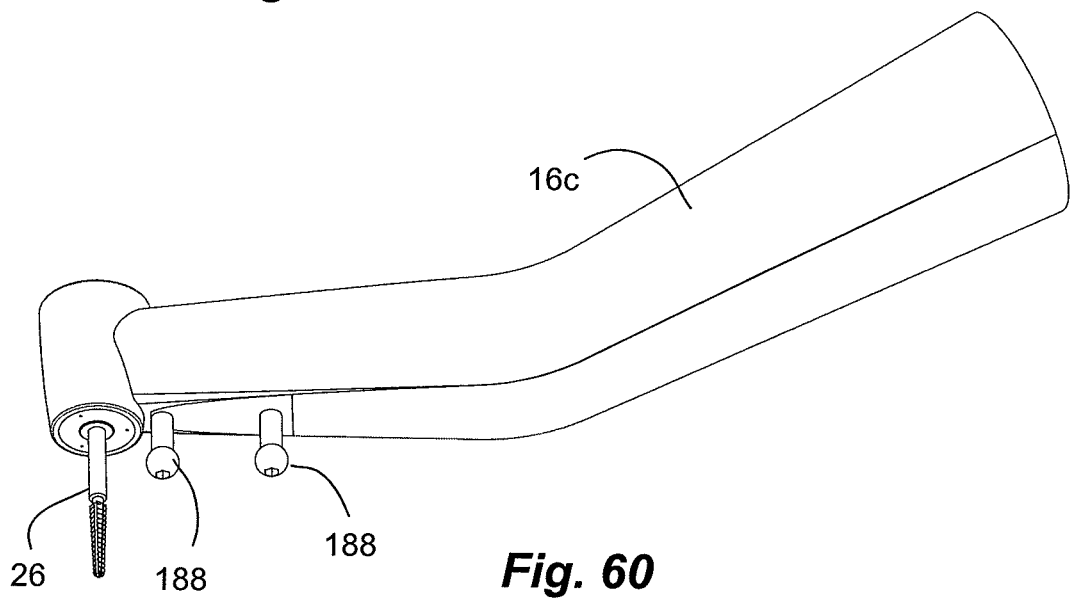
FIG. 60 is a perspective view of the handpiece of FIG. 59.
Figure 61:
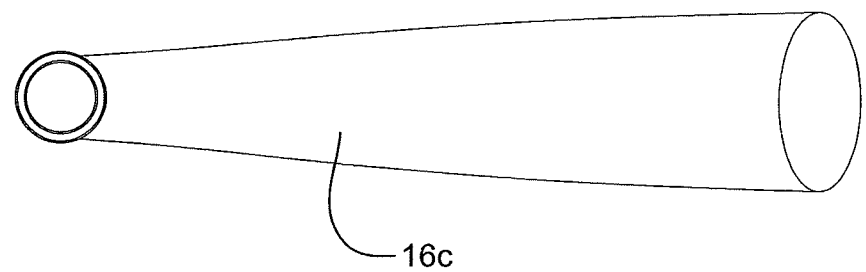
FIG. 61 is a top view of the handpiece of FIG. 59.
Figure 62:
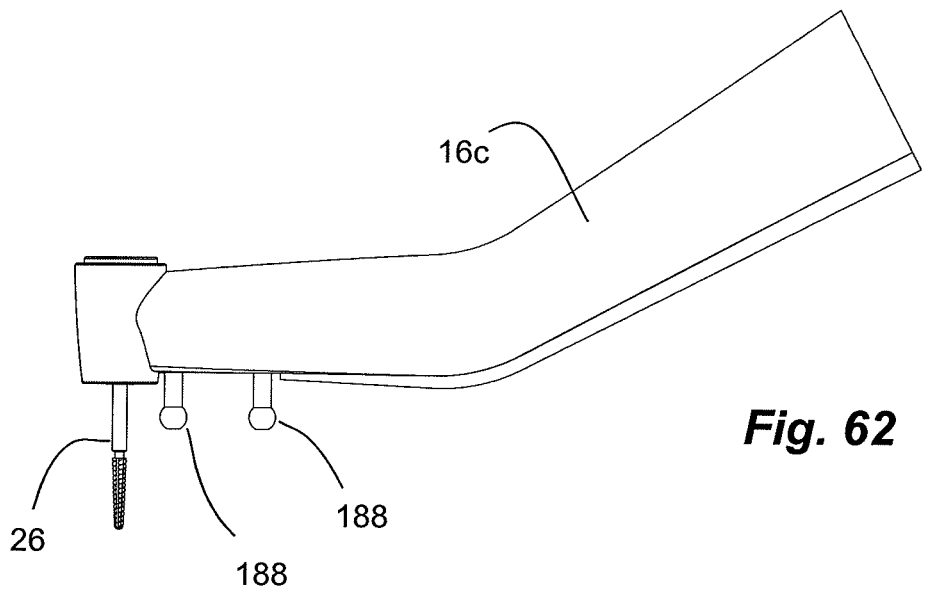
FIG. 62 is a side view of the handpiece of FIG. 59.
Figure 63:
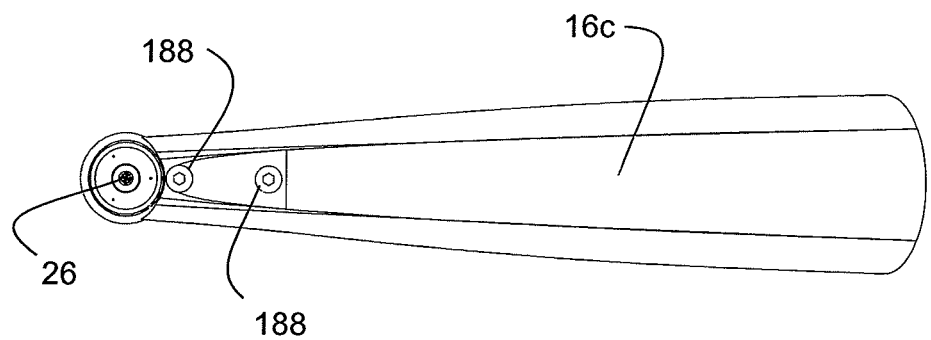
FIG. 63 is a bottom view of the handpiece of FIG. 59.
Figure 64:
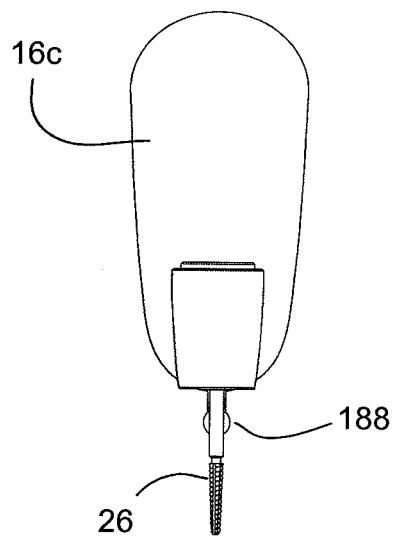
FIG. 64 is an end view of the handpiece of FIG. 53.
Figure 65:
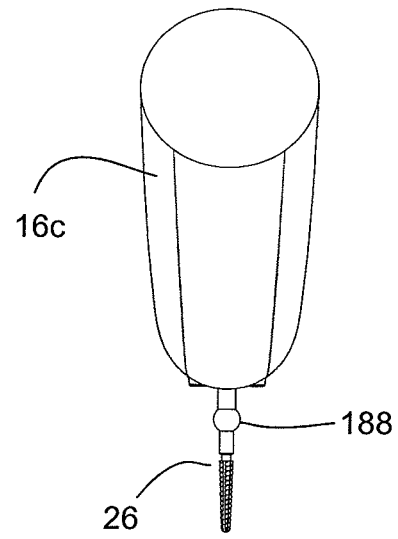
FIG. 65 is an end view of the handpiece of FIG. 53.

The cutting system 10 can include at least one cutting guide or a plurality of cutting guides. A single cutting guide may be used for cutting a tooth to receive an inlay or a veneer. One or more cutting guides may be used for cutting a tooth to receive a crown, or for cutting adjacent teeth to receive a bridge. (Two cutting guides are shown in FIGS. 1 and 18 for cutting a tooth to receive a crown; while one cutting guide is shown in FIG. 37 for cutting a tooth to receive a crown.) Each cutting guide can have one or more slots to guide the cutting tool to make one or more cuts in the tooth. Referring to FIGS. 17, 24 and 25, each cutting guide, indicated generally at 40, can have at least one cavity 44 to match at least a portion of at least one of a patient's teeth 14b (FIG. 7) inside a patient's mouth. In one aspect, the cavity can be sized and shaped to receive at least a portion of one or more adjacent teeth 14b adjacent to, and/or laterally and/or longitudinally remote from, the tooth 14 to be cut. Thus, the cutting guide is located laterally and/or longitudinally adjacent to and laterally and/or longitudinally remote from the tooth to be cut, rather than over or obscuring the tooth to be cut, so that the tooth to be cut is exposed with respect to the cutting guide. In one aspect, the entire tooth to be cut is exposed with respect to the cutting guide. In another aspect, the cavity can be sized and shaped to receive at least a portion of the tooth to be cut. At least a portion of the cavity or walls thereof can be shaped to match or mate with the patient's teeth 14b. The cutting guide and cavity thereof can be custom made for the patient based on a scan of the patient's teeth or mouth, or impression or model thereof. The cutting guide can have buccal, lingual and occlusal walls abutting or located adjacent to or proximal to the respective buccal, lingual and occlusal surface or side of the tooth or teeth. In addition, the cutting guide may include a mesial and/or distal wall abutting or located adjacent to or proximal to the respective mesial and distal surface or side of the tooth or teeth. In the case of multiple cutting guides, each cutting guide can be separately located on the at least a portion of teeth inside the patient's mouth that are adjacent to, and/or remote from, the patient's tooth to be cut.

In addition, each cutting guide 40 can have at least one slot, indicated generally at 48, in the cutting guide with a depth extending from an exterior of the cutting guide into the cutting guide. The slots can be channels or grooves formed in the cutting guide with exterior openings and closed interiors. The slots have a cross-sectional shape (transverse to a longitudinal length of the slot) with a narrower exterior or opening and an enlarged interior or cavity, such as a keyhole. In one aspect, the slots can extend only partially into the cutting guide without extending to the cavity therein. In one aspect, the slots can include three slots, as shown in FIGS. 1 and 3-29. In another aspect, the slots can include two slots, as shown in FIGS. 37 and 39-51. In addition, the slots can be provided in groups, and the cutting guide can have a plurality of groups of slots, each having a plurality of slots, with each of the plurality of groups of slots disposed on a different side or face of the at least one cutting guide, as shown in FIGS. 18-29, 37 and 39-51. Again, the configuration, location and/or orientation of the slot(s) 48 can be custom made for the patient based on the prosthesis or restoration and cut model of the tooth. The slots can define a cutting path or path of travel for the cutting tool, such that moving the guide pins along the slots properly positions and orients the cutting tool or burr to cut and shape the tooth to form a cut tooth in a predetermined shape and size (as previously modeled) to receive a prosthetic or restoration (also as previously modeled). The slots form or define a laterally and/or longitudinally remote cutting path corresponding to, but remote from, an actual cutting path of the cutting burr on the patient's tooth to be cut. Thus, the slots can be spaced-apart from the tooth to be cut in a lateral (buccal and/or lingual) direction, or a longitudinal (mesial and/or distal) direction. The slots, or bottoms thereof, can have an elevational height with respect to the teeth that can vary or change along the slots to vary or change, and thus control, a depth of cut of the cutting tool. The cutting guide can comprise plastic, and be formed with 3D printing on a 3D printer, or milled or machined, or the like, to create the cutting guide with the slot(s) and cavity therein.

As described above, the system 10 can include at least one cutting guide or a plurality of cutting guides depending on the cut(s) to be made, and the restoration to be performed or installed. In the case of an inlay or a veneer, a single cutting guide may be used. For an inlay, a single cutting guide may be used with a single slot in the occlusal wall of the cutting guide to cut an occlusal surface or side of the tooth to receive the inlay. Similarly, for a veneer, a single cutting guide may be used with a single slot in the occlusal wall of the cutting guide to cut a buccal wall of the tooth or teeth to receive the veneer. In the case of a bridge, one or more cutting guides may be used, each with one or more slots, to cut the teeth to receive the bridge. Similarly, in the case of a crown, one or more cutting guides can be used.

The present invention will be described with respect to a crown with the understanding that such description is applicable to other cases, such as inlays, veneers and bridges. Thus, the plurality of cutting guides can include two cutting guides, namely: a buccal, lingual, mesial and/or distal cutting guide 40*b* for cutting a buccal, lingual, mesial and/or distal surface or side of the tooth 14, as shown in FIGS. 1 and 3-17; and an occlusal cutting guide 40*c* for cutting an occlusal surface or side of the tooth 14, as shown in FIGS. 18-29. In another aspect, more than one cutting guide can be used to cut the buccal, lingual, mesial and/or distal surface or sides of the tooth.

The buccal, lingual, mesial and/or distal cutting guide 40*b* (FIGS. 1 and 3-17), for cutting the buccal, lingual, mesial and/or distal side or surface of the tooth 14, can have one or more buccal, lingual, mesial and/or distal slots 48*b* located in and/or on the occlusal wall of the cutting guide, and corresponding to the buccal, lingual, mesial and/or distal surface or side of the tooth 14. Each of the slots 48*b* can be annular and can form a continuous loop to guide the cutting burr in a continuous annular loop around the tooth 14 to cut all of the buccal, lingual, mesial and/or distal surface or side of the tooth. In another aspect, the buccal, lingual, mesial and/or distal slot can be separated into different segments in different cutting guides. For example, a first buccal and lingual cutting guide can have buccal and lingual slots to cut buccal and lingual sides of the tooth; while a second mesial and distal cutting guide can have mesial and distal slots to cut mesial and distal sides of the tooth. As another example, a buccal and mesial (or buccal and distal) cutting guide can have buccal and mesial (or buccal and distal) slots to cut buccal and mesial (or buccal and distal) sides of the tooth; while a lingual and distal (or lingual and mesial) cutting guide has lingual an distal (or lingual and mesial) slots to cut lingual and distal (or lingual and mesial) sides of the tooth. As described above, the cutting guide 40*b* can be disposed on teeth adjacent to, and remote from, the tooth 14 to be cut so that the tooth can be viewed during cutting. Similarly, one or more such cutting guides can be used to cut adjacent but separated teeth to receive a bridge. In addition, such a cutting guide can be used to cut the buccal side or surface of a tooth to receive a veneer. Furthermore, such a cutting guide can also be configured to cut the occlusal surface or side of the tooth to receive an inlay.

The occlusal cutting guide 40*c* (FIGS. 18-29), for cutting the occlusal side or surface of the tooth, can have opposite groups of occlusal slots 48*c* located laterally on the occlusal cutting guide. Some of the occlusal slots can be located on the buccal side or wall of the cutting guide, while the other occlusal slots can be located on the lingual side or wall of the cutting guide, opposite one another on the cutting guide. Some of the occlusal slots can be formed on the occlusal wall of the cutting guide. The occlusal slots 48*c* can be oriented at an incline with an acute angle with respect to a plane of the occlusal side of the tooth, and located to extend the cutting burr approximately midway into the occlusal surface of the tooth, to form a V-shaped cut with an obtuse angle (for purposes of receiving a crown). As described above, the cutting guide 40*c* can be disposed on teeth adjacent to, and remote from, the tooth 14 to be cut so that the tooth can be viewed during cutting. Again, one or more such occlusal cutting guides can be used to cut adjacent but separated teeth to receive a bridge. Each cutting guide can comprise a main body 62 configured to engage at least one of a patient's teeth, including a buccal wall 64, a lingual wall 66 and an occlusal wall 68. Each cutting guide can comprise a protrusion(s) 70 extending from the main body 62 and having the slot (48*b*, 48*c*) therein. The protrusion 70 can have a wall 72 surrounding a majority of the slot with a constant cross-sectional shape, as shown in FIGS. 28, 29, 39, 40, 50 and 51. In addition, the cutting guide can include a mesial 74 and/or a distal wall 76 abutting or located adjacent to or proximal to the respective mesial and distal surface or side of the tooth or teeth.

Referring to FIGS. 28, 29, 39, 40, 50 and 51, the slots 48 (and 48*b*, 48*c*) can have a cross-sectional shape (taken transverse to a longitudinal length of the slot) with a narrower exterior or opening 78 and an enlarged interior or cavity 80. Thus, the slots have a greater width in the interior or bottom, and a smaller width at the exterior or opening. The slots can have a keyhole-shaped cross-section or profile. The narrower exterior or opening can have opposing, substantially parallel walls, while the enlarged interior or cavity can have a circular or round cross-section shape or profile.

Figure 2:
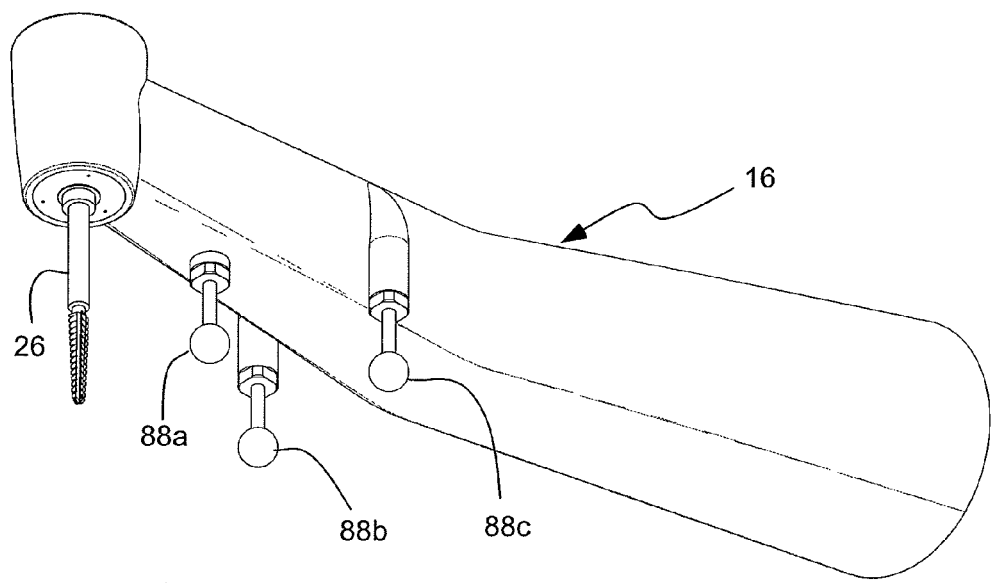
FIG. 2 is a perspective view of the handpiece of the dental cutting system of FIG. 1.
Figure 3:
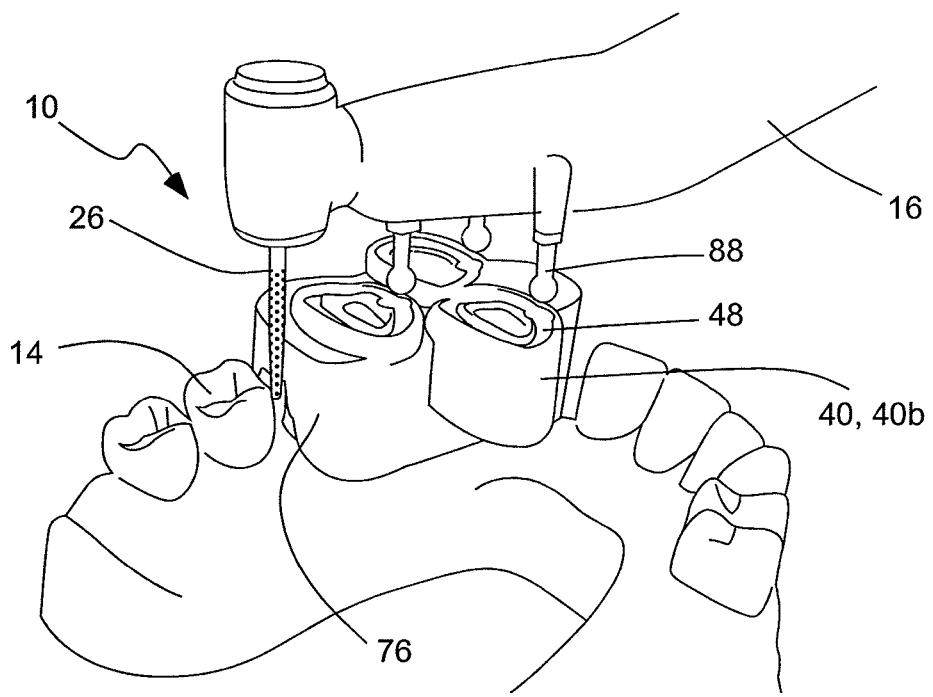
FIG. 3 is a perspective view of the dental cutting system of FIG. 1, shown with the handpiece or guide pins thereof removed from the cutting guide.
Figure 4:
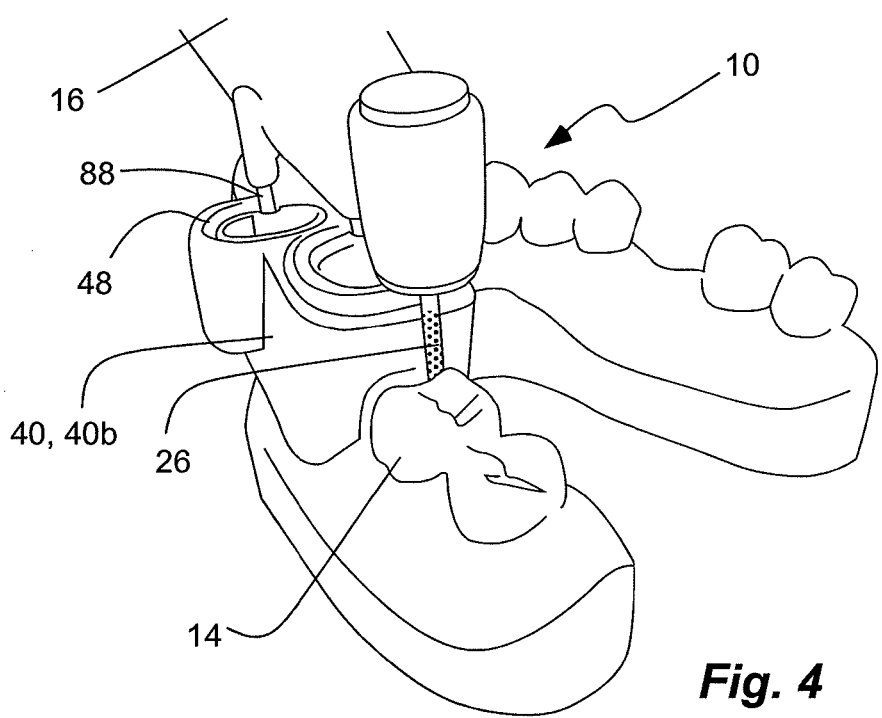
FIG. 4 is a perspective view of the dental cutting system of FIG. 1.
Figure 5:
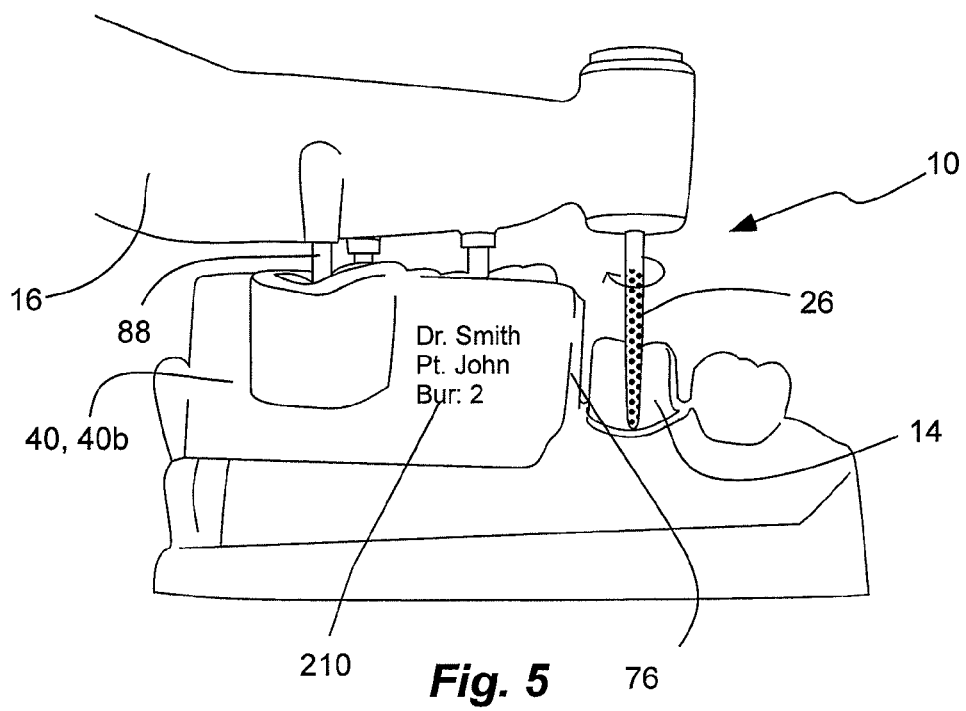
FIG. 5 is a side view of the dental cutting system of FIG. 1.
Figure 6:
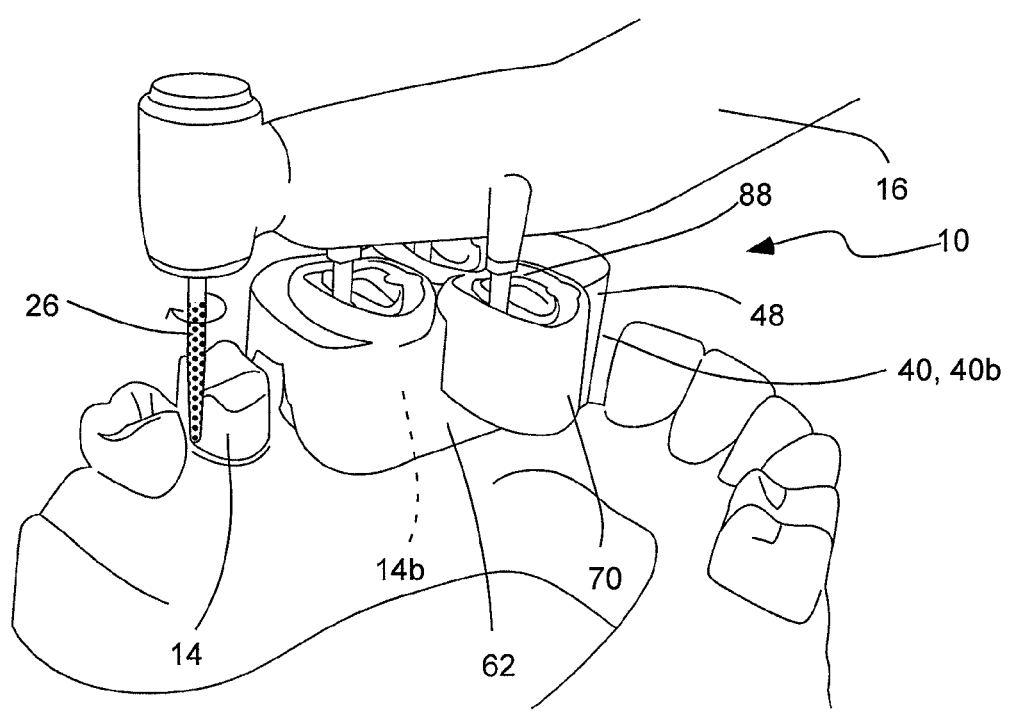
FIG. 6 is a perspective view of the dental cutting system of FIG. 1.
Figure 7:
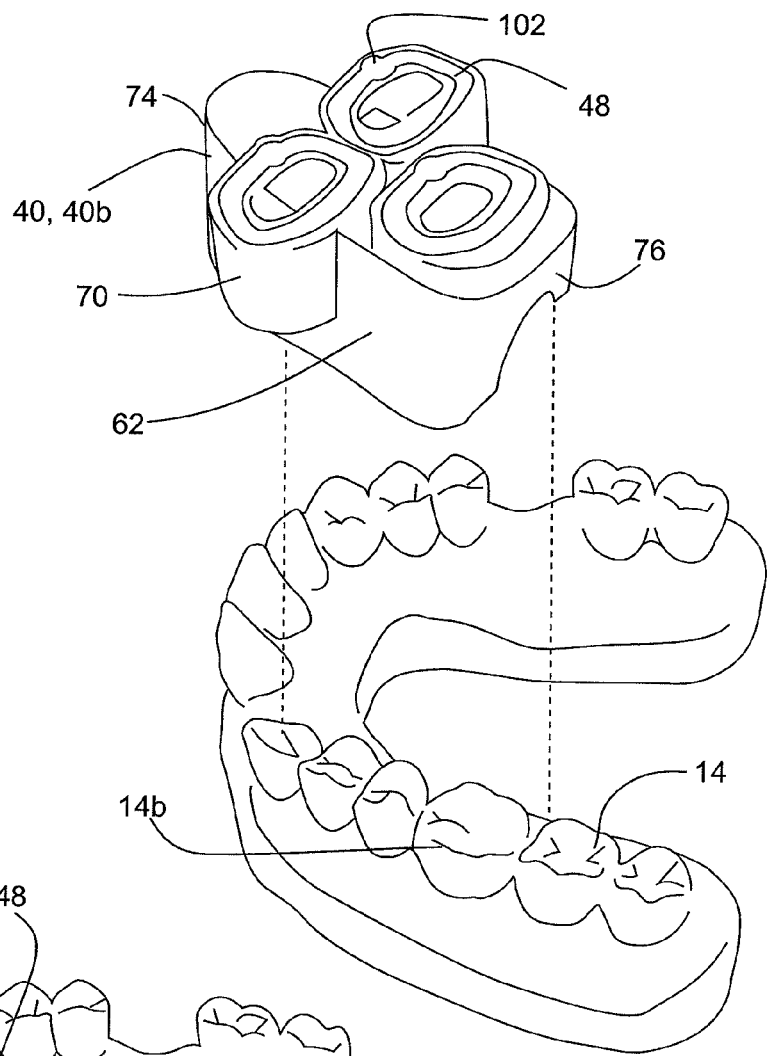
FIG. 7 is a perspective view of the dental guide of the dental cutting system of FIG. 1, shown removed from a patient's teeth.
Figure 8:
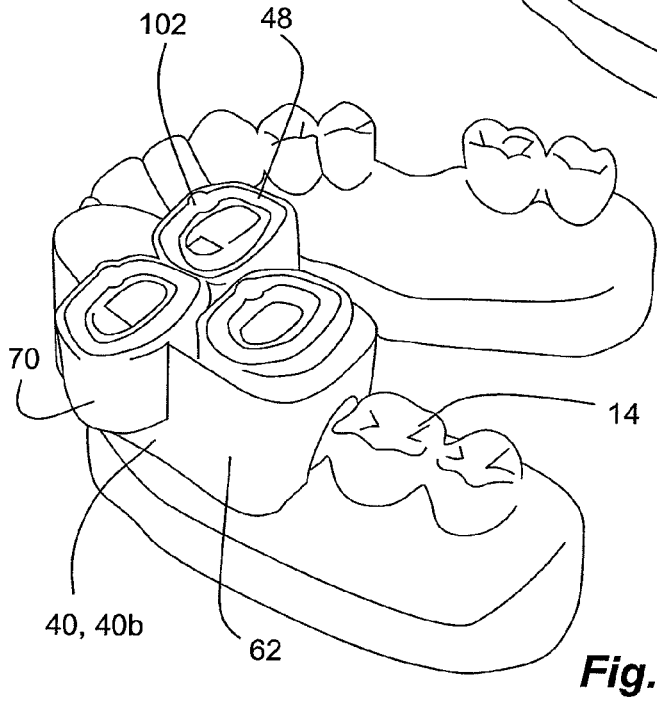
FIG. 8 is a perspective view of the dental guide of the dental cutting system of FIG. 1, shown placed on the patient's teeth.
Figure 14:
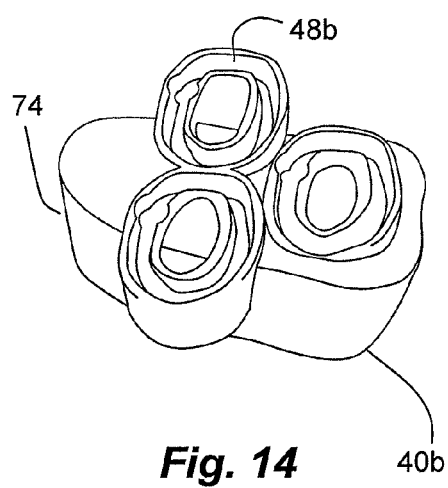
FIG. 14 is a perspective view of the dental guide of the dental cutting system of FIG. 1.
Figure 15:
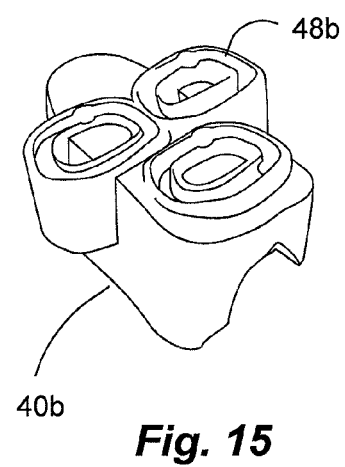
FIG. 15 is a perspective view of the dental guide of the dental cutting system of FIG. 1.
Figure 16:
FIG. 16 is an end view of the dental guide of the dental cutting system of FIG. 1.
Figure 32:
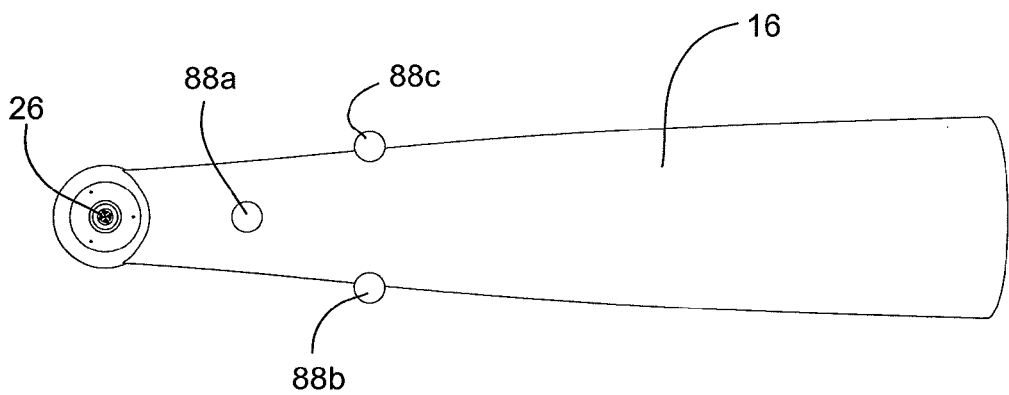
FIG. 32 is a bottom view of the handpiece of FIG. 31.
Figure 33:
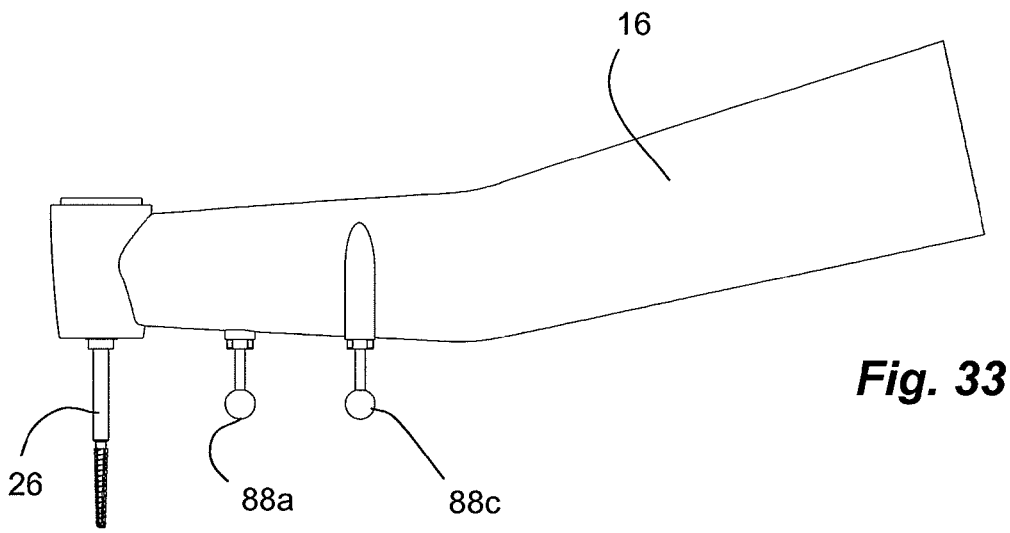
FIG. 33 is a side view of the handpiece of FIG. 31.
Figure 34:
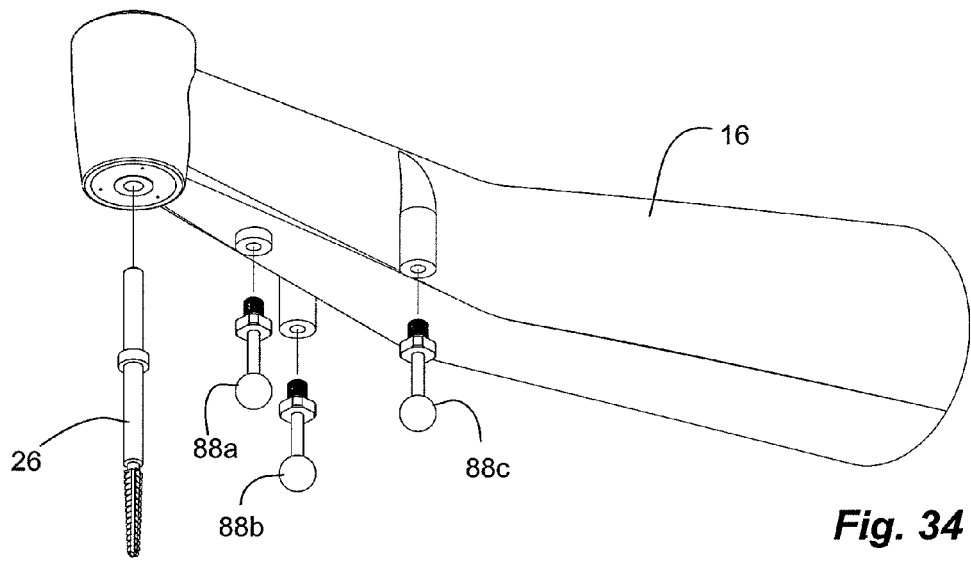
FIG. 34 is an exploded perspective view of the handpiece of FIG. 31.
Figure 35:
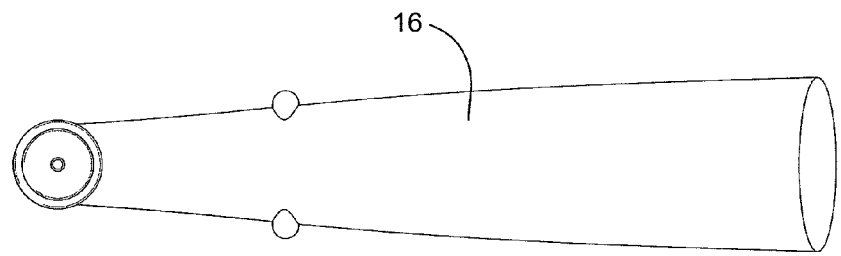
FIG. 35 is a bottom view of the handpiece of FIG. 31.
Figure 36:
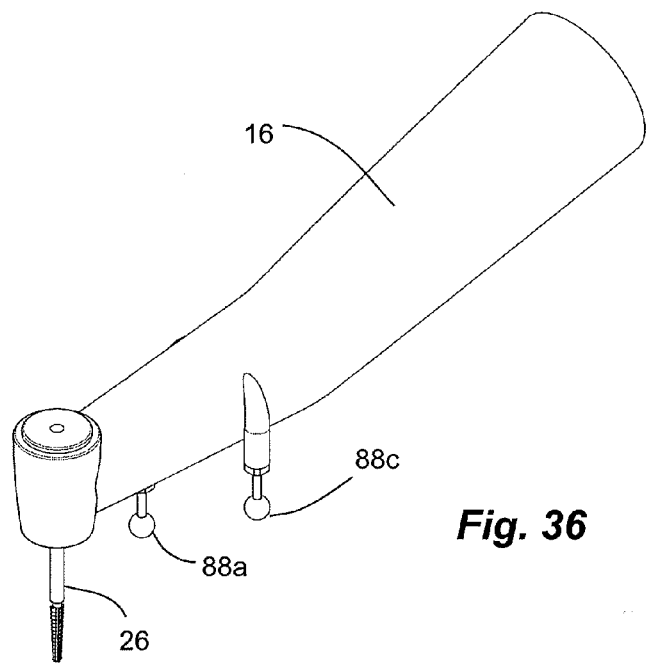
FIG. 36 is a perspective view of the handpiece of FIG. 31.

The dental handpiece 16 can have and can carry a plurality of guide pins 88 attached to and extending from the handpiece, and located laterally and/or longitudinally remote from the cutting tool 18 and the cutting burr 26. The guide pins can be located remote from the cutting burr and cutting tool in the lateral and/or longitudinal direction with respect to a longitudinal axis of the handpiece, and also in the buccal/lingual and/or mesial/distal direction with respect to the patient's tooth to be cut. The guide pins 88 can be directly coupled to and affixed to the handpiece 16 and the shank or handle thereof, and spaced-apart from the cutting burr 26, head and chuck. The guide pins 88 can be disposed on the shank or handle of the handpiece, laterally and/or longitudinally remote from the cutting burr, head and chuck, and thus can correspond to the location of the cutting guide so that the tooth to be cut is exposed with respect to the cutting guide, and the cutting tool and tooth to be cut can be viewed by the dental profession during cutting. In one aspect, the guide pins can be located on the shank or handle of the handpiece away from the head in a direction of the proximal end of the handpiece. Thus, the guide pins can be located aft or rearward of the head. The guide pins can be removably coupled to the handpiece, or the shank or handle thereof, so that they can be removed and replaced. The guide pins 88 can extend transverse to a longitudinal axis of the handpiece, and parallel with the cutting tool or cutting burr. In one aspect, the plurality of guide pins can include three guide pins, each corresponding to a different one of three slots, as shown in FIGS. 1-36. In another aspect, the plurality of guide pins can include two guide pins, each corresponding to a different one of two slots, as shown in FIG. 37-68. The three guide pins can be arrayed in a triangle, as shown in FIGS. 2 and 32. The three guide pins can include a center guide pin 88a aligned with the cutting burr 26 on the handpiece, shank or handle (with respect to a longitudinal axis of the handpiece), and a pair of lateral guide pins 88b and 88c disposed laterally with respect to the center guide pin 88a (and the longitudinal axis of the handpiece). In one aspect, one or more of the guide pins and the cutting burr can be off axis or unaligned with respect to one another. Three guide pins and/or the triangular or lateral configuration of the guide pins can provide lateral and longitudinal stability of the handpiece, and thus the cutting burr.

Referring to FIGS. 30a-e, the guide pins 88 can have a proximal end attached to the handpiece with a narrower neck or stem 90, and can extend to a distal, free end with an enlarged head or orb 92. The proximal end of the neck or stem can be directly coupled to and attached to and affixed to the handpiece. The proximal end can be threaded to couple to a threaded bore in the body of the handpiece. A nut can be integral with the pin or neck thereof adjacent the proximal ends and the threads to facilitate coupling and removal of the pins from the handpiece. The guide pins 88 have a shape or profile, and size, that match a cross-sectional shape or profile of the corresponding slots 48, so that the guide pins and the slots mate or match. Thus, the neck or stem can be cylindrical to match the parallel opposing walls of the narrower exterior or opening of the slot, and the head or orb can be spherical to match the round shape or profile of the enlarged interior or cavity of the slots. The shape or profile of the slots and the guide pins can also retain the guide pins in the slots, and thus control the elevational height of the guide pins, and thus depths of cut of the cutting tool, with respect to the teeth. Thus, the narrower exterior or opening of the slot retains the enlarged head of the guide pin in the slot to maintain the elevational height of the guide pin with respect to the teeth, and maintain the depth of cut of the cutting tool. The guide pins are slidable in the slots to guide the cutting burr along the cutting path with respect to the patient's tooth to be cut. The guide pins are separate from the cutting burr, and remove the high speed revolutions of the cutting tool from the cutting guide so that the guide pins slide in the slots, without rotating or spinning like the cutting burr. The guide pins, or neck and head thereof, can be a single, monolithic body formed together. The guide pins can be metallic and formed from metal, such as brass.

In one aspect, the cutting guides or the slots thereof can have an enlarged opening 102 formed in the slot, or the narrower exterior or opening thereof. Thus, the guide pins 88 or enlarged heads can be inserted into the slots through the enlarged opening 102. In one aspect, the guide pins can be inserted into the slots prior to activating the cutting tool. In another aspect, the cutting tool can be activated prior to inserting the guide pins into the slots. In one aspect, the slot can be configured so that the cutting tool or burr is initially located outside the perimeter of the tooth, and the cutting tool can be moved to cut the tooth in a sweeping motion.

A method for cutting a patient's tooth 14, and utilizing the system 10 described above, comprises: placing the cutting guide (40, 40b, 40c) on at least one of the patient's teeth 14b with the cavity 44 of the cutting guide matching at least a portion of at least one of the patient's teeth while leaving the patient's tooth to be cut exposed with respect to the cutting guide, and at a location remote from the patient's tooth to be cut; inserting the enlarged head or orb 92 of each of the plurality of guide pins 88 (88a-c) into a different one of the plurality of slots 48 (48b, 48c) in the at least one cutting guide; displacing the plurality of guide pins 88 (88a-c) along the plurality of slots 48 (48b, 48c) to guide the cutting burr 26 and displace the cutting burr with respect to the tooth 14 to be cut. The cutting guide can be removed and a prosthetic or restoration affixed to the user's cut tooth. Another cutting guide can be subsequently placed on the patent's teeth, and subsequent cuts made. For example, the buccal, lingual, mesial and/or distal cutting guide 40b can be placed on the user's teeth to make buccal, lingual, mesial and/or distal cuts in the buccal, lingual, mesial and/or distal face of the tooth. The buccal, lingual, mesial and/or distal cutting guide 40b can be removed and the occlusal cutting guide 40c can be placed on the user's teeth to make occlusal cuts in the occlusal face of the tooth. The cuts can also be made in the opposite order.

As described above, the method can further comprise: obtaining a 3D image or model of the patient's teeth; digitally preparing a tooth to be cut based on the 3D image; digitally designing a restoration; digitally designing the cutting guide; and producing the cutting guide and the restoration. The 3D image can be obtained from scanning the patient's teeth directly; scanning an impression of the patient's teeth; or scanning a model of the patient's teeth made from the impression. The 3D scan can be or can be used to create a digital model of the patient's teeth. The cuts can be modeled on the digital model of the patient's teeth with a digital model of the cutting tool and/or burr. In addition, a digital model of the cut tooth can be created or prepared. A prosthesis or restoration can be designed digitally using the digital model of the cut tooth, and the digital model of the patient's teeth, to create a digital model of the prosthesis or restoration. In addition, the cutting guide(s) can be designed and modeled using the model of the patient's teeth, the digital model of the tooth to be cut, and the digital model of the cutting tool and/or bur, to create a digital model of the cutting guide. The cutting guide(s) can be produced using 3D printing or milling. The prosthesis can be produced by milling or machining. The system can include one or more computer system with executable instructions to control the above.

Referring to FIGS. 37-58, another dental cutting system 10b is shown that is similar in many respects to that described above, and which description is hereby incorporated herein by reference. The cutting system can include a single cutting guide 140 with multiple groups of slots, with each group including a pair of slots. In addition, the cutting system can include a handpiece 16b with a pair of guide pins 188. The cutting system and the cutting guide are configured, by way of example, to prepare or cut a tooth to receive a crown.

The cutting guide 140 includes a pair of buccal, lingual, mesial and/or distal slots 148b on an occlusal wall of the cutting guide to cut a buccal, lingual, mesial and/or distal face of the tooth; a first pair of occlusal slots 148c disposed on a buccal wall of the cutting guide to cut a first portion of an occlusal face of the tooth; and a second pair of occlusal slots 148c disposed on a lingual wall of the cutting guide to cut a second portion of the occlusal face of the tooth. Each pair of slots can include fore and aft slots.

The pair of guide pins 188 can include fore and aft guide pins. The guide pins 188 and the cutting burr 26 can be off axis or unaligned with respect to one another to provide stability and maintain the desired orientation of the cutting burr.

Referring to FIGS. 52a-e, the guide pins 188 can have a proximal end attached to the handpiece with a narrower neck or stem 190, and can extend to a distal, free end with an enlarged head or orb 192. The proximal end of the neck or stem can be directly coupled to and attached to and affixed to the handpiece. The proximal end can be threaded to couple to a threaded bore in the body of the handpiece. An indentation can be formed in the head and aligned with the stem, such as a hex bolt receiver, to facilitate coupling and removal of the pins from the handpiece.

Referring to FIGS. 59-65, another dental cutting system is shown that is similar in many respects to that described above, and which description is hereby incorporated herein by reference. The cutting system can include a handpiece 16c with a pair of guide pins 188. The pair of guide pins 188 can include fore and aft guide pins that can be aligned with respect to the cutting burr 26.

Figure 66:
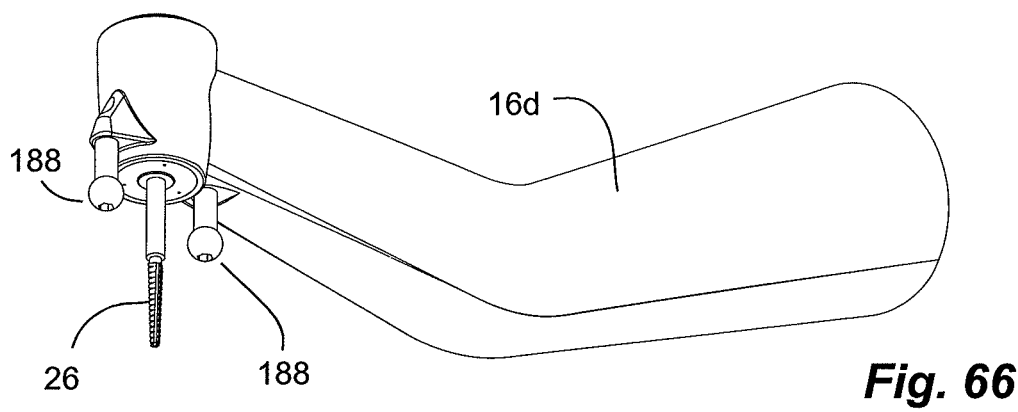
FIG. 66 is a perspective view of another handpiece in accordance with another embodiment of the present invention.
Figure 67:
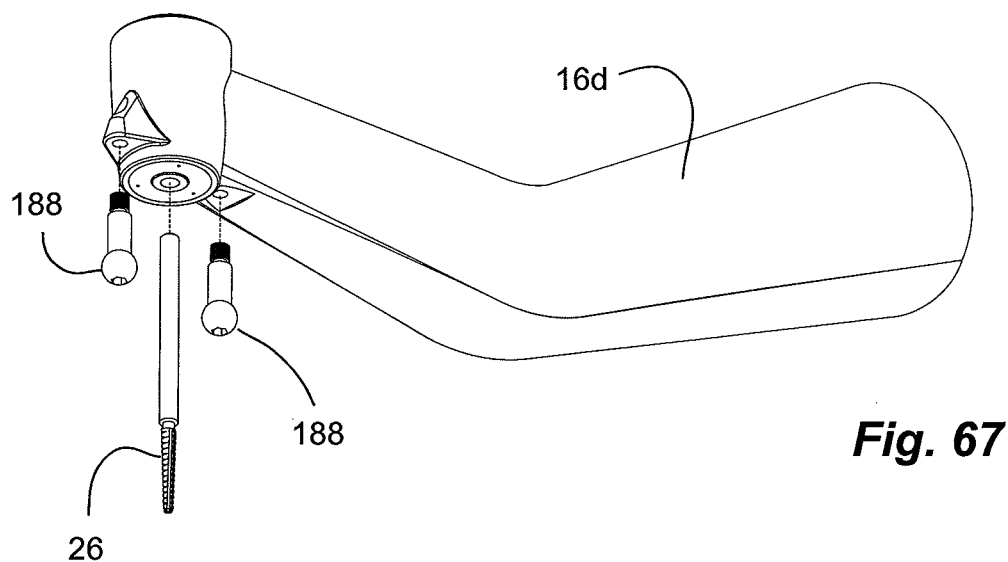
FIG. 67 is an exploded perspective view of the handpiece of FIG. 66.

Referring to FIGS. 66-68, another dental cutting system is shown that is similar in many respects to that described above, and which description is hereby incorporated herein by reference. The cutting system can include a handpiece 16d with a pair of guide pins 188. The pair of guide pins 188 can include fore and aft guide pins that can be disposed on opposite sides of the cutting burr 26, as opposed to the same side of the cutting burr.

Referring to FIGS. 16, 17, 23-25 and 50, the cutting guides described above can also include one or more undercut bumps 200 in the cavity of the cutting guide. The undercut bumps 200 can be formed on an interior buccal surface or wall of the cutting guide, near or adjacent a bottom of the cutting guide corresponding to a bottom of the patient's teeth on the tooth where the tooth meets the gum. The bumps can extend inwardly into the cavity from the inner wall or surface. In one aspect, the bumps can be formed on the buccal wall. In another aspect, the bumps can be formed on the lingual wall. In addition, the cutting guide or the cavity thereof can be sized with a larger opening or straighter interior walls or surfaces than the user's teeth to allow the cutting guide to be placed on the patient's teeth with the teeth received through the opening to the cavity. The cutting guide can be relatively rigid. The undercut bumps can abut or be placed against one or more teeth and can help hold the cutting guide in place on the user's teeth while a dental professional perform the dental restoration procedure. Thus, the undercut bumps can provide a snap fit or interference or press fit on the patient's teeth. Temporary cement or another adhesive may also be used with the cutting guide to ensure that the cutting guide remains stationary throughout the cutting procedure.

In addition, any of the cutting guides described above can further comprise indicia 210 (FIGS. 5, 21 and 26) or engraving disposed thereon that is indicative of, or indicated, pertinent information, such as doctor name, patient name, bur number, etc. The indicia can facilitate organization, storage and/or location of the cutting guide. The indicia can be formed directly on the cutting guide and of the same material as the cutting guide. In addition the indicia can be formed at the same time as and integrally with the cutting guide, such as by 3D printing, such that the indicia and the cutting guide form a single, unitary, monolithic body. In one aspect, the indicia can protrude from a surface of the cutting guide. In another aspect, the indicia can extend into the cutting guide.

In addition, the cutting guides can include a shelf extending from the cutting guide or lateral wall thereof adjacent to the slots, and extending beyond the slots, to receive a head of the handpiece, and/or to separate the patient's tongue from the handpiece and cutting tool. The cutting guides described above can also include a shelf or guard.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A dental cutting system for cutting a patient's tooth, the system comprising:
   a) at least one cutting guide having at least one cavity configured to match at least a portion of at least one of a patient's teeth inside a patient's mouth adjacent to or remote from the patient's tooth to be cut without covering the patient's tooth to be cut and exposing the patient's tooth to be cut;
   b) a plurality of slots in the cutting guide extending from an exterior of the cutting guide into the cutting guide;
   c) each of the plurality of slots having a cross-sectional shape with a narrower exterior between opposing walls and an enlarged interior with a circular cross-sectional shape;
   d) a handpiece configured to be held and carrying a cutting tool with a cutting burr configured to cut the patient's tooth;
   e) a plurality of guide pins attached to and extending from a handle of the handpiece and located remote from and spaced-apart from a head and the cutting burr of the handpiece;
   f) each of the plurality of guide pins having a narrower neck with a cylindrical shape and an enlarged head with a spherical shape, the cross-sectional shape of the plurality of slots having a size and a shape that matches and mates with a cross-sectional profile of the plurality of guide pins and with the cylindrical shape of the enlarged head matching and mating with the circular cross-sectional shape of the enlarged interior; and
   g) the plurality of guide pins being slidable in the plurality of slots to guide the cutting burr with respect to the patient's tooth to be cut, the plurality of slots defining a remote cutting path for the cutting burr corresponding to, but remote from, an actual cutting path of the cutting burr on the patient's tooth to be cut, such that displacing the plurality of guide pins along the plurality of slots displaces the cutting burr along the cutting path to cut and shape the patient's tooth to be cut to form a cut tooth in a predetermined shape and size.

2. The system in accordance with claim 1, wherein each of the plurality of slots extends only partially into the cutting guide without extending to the at least one cavity therein.

3. The system in accordance with claim 1, wherein the plurality of slots includes three slots and the plurality of guide pins includes three guide pins each corresponding to a different one of the three slots.

4. The system in accordance with claim 3, wherein the three guide pins are arrayed in a triangle.

5. The system in accordance with claim 4, wherein the three guide pins include a center guide pin aligned with the cutting burr on the cutting tool, and a pair of lateral guide pins disposed laterally with respect to the center guide pin.

6. The system in accordance with claim 1, further comprising a plurality of groups of slots each having a plurality of slots, with each of the plurality of groups of slots disposed on a different side or face of the at least one cutting guide.

7. The system in accordance with claim 1, wherein the plurality of guide pins and the cutting burr are off axis or unaligned with respect to one another.

8. The system in accordance with claim 1, wherein the at least one cutting guide includes a main body configured to engage at least one of a patient's teeth including buccal, lingual and occlusal walls; and wherein the at least one cutting guide includes protrusions extending from the main body and having the plurality of slots therein, with the protrusions having a wall surrounding a majority of a slot with the wall having a substantially constant cross-sectional shape.

9. The system in accordance with claim 1, wherein the at least one cutting guide further comprises a plurality of cutting guides each being separately located on the at least a portion of teeth inside the patient's mouth that are adjacent to or remote from the patient's tooth to be cut, and each having a plurality of slots corresponding to the plurality of guide pins.

10. The system in accordance with claim 1, wherein the at least one cutting guide is an occlusal cutting guide, and the plurality of slots includes three occlusal slots located on a buccal side of the occlusal cutting guide, and three occlusal slots located on a lingual side of the occlusal cutting guide.

11. The system in accordance with claim 1, wherein the at least one cutting guide is a buccal cutting guide, or a lingual cutting guide, or both, and the plurality of slots includes three buccal slots, or three lingual slots, or both, located on an occlusal wall.

12. The system in accordance with claim 1, wherein the at least one cutting guide includes at least one undercut bump extending from an interior surface of the at least one cutting guide and into the cavity configured to abut to a patient's tooth.

13. The system in accordance with claim 1, wherein the at least one cutting guide includes indicia formed directly thereon and integrally with the at least one cutting guide.

14. A method for cutting a patient's tooth utilizing the system in accordance with claim 1, the method comprising:
    a) placing the at least one cutting guide on the least one of the patient's teeth with the cavity of the cutting guide matching at least a portion of at least one of the patient's teeth while leaving the patient's tooth to be cut exposed;
    b) inserting the enlarged head of each of the plurality of guide pins into a different one of the plurality of slots in the at least one cutting guide; and
    c) displacing the plurality of guide pins along the plurality of slots to guide the cutting burr and displace the cutting burr with respect to the tooth to be cut.

15. The method in accordance with claim 14, further comprising, under the control of one or more computer systems configured with executable instructions:
    a) obtaining a 3D image or the patient's teeth;
    b) digitally preparing a tooth to be cut based on the 3D image;
    c) digitally designing a restoration;
    d) digitally designing the cutting guide; and
    e) producing the cutting guide and the restoration.

16. The system in accordance with claim 1, wherein the cutting burr and the guide pins extend transverse to a longitudinal axis of the handpiece.

17. The system in accordance with claim 1, wherein the plurality of slots are oriented transverse to an axis of the cutting burr when the plurality of guide pins are in the plurality of slots, such that displacing the plurality of guide pins along the plurality of slots displaced the cutting burr transverse to the axis of the cutting burr.

18. A dental cutting system for cutting a patient's tooth, the system comprising:
    a) a plurality of cutting guides each having at least one cavity therein coinciding with at least a portion of teeth inside a patient's mouth that are adjacent to or remote from the patient's tooth to be cut without covering the patient's tooth to be cut to expose the patient's tooth to be cut with respect to the cutting guide;
    b) each of the plurality of cutting guides comprising a plurality of slots in the cutting guide extending from an exterior of the cutting guide into the cutting guide;
    c) each of the plurality of slots having a cross-sectional shape with a narrower exterior between opposing walls and an enlarged interior with a circular cross-sectional shape;
    d) the plurality of cutting guides comprising:
       1) an occlusal cutting guide with occlusal slots located laterally on the occlusal cutting guide;
       2) a buccal cutting guide, or a lingual cutting guide, or both, with buccal slots, or lingual slots, or both, located on an occlusal wall of the cutting guide;
    e) a handpiece with a handle configured to be held and a head with a cutting tool with a cutting burr configured to cut the patient's tooth;
    f) a plurality of guide pins attached to and extending from the handle of the handpiece and located remote from and spaced-apart from the cutting burr and the head;
    g) each of the plurality of guide pins having a narrower neck with a cylindrical shape and an enlarged head with a spherical shape, the cross-sectional shape of the plurality of slots having a size and a shape that matches and mates with a cross-sectional profile of the plurality of guide pins and with the cylindrical shape of the enlarged head matching and mating with the circular cross-sectional shape of the enlarged interior; and
    h) the plurality of guide pins being slidable along the plurality of slots to displace the cutting burr with respect to the patient's tooth to be cut.

19. A cutting tool device for cutting a patient's tooth, the device comprising:
    a) a handpiece with a handle configured to be held and having a head with a cutting burr configured to cut the patient's tooth;
    b) a plurality of guide pins attached to and extending from the handle of the handpiece and located remote from and spaced-apart from the cutting burr and the head;
    c) the cutting burr and the plurality of guide pins extending transverse to a longitudinal axis of the handpiece;
    d) the guide pins having a narrower neck with a cylindrical shape and an enlarged head with a spherical shape;
    e) at least one cutting guide having at least one cavity to match at least a portion of at least one of a patient's teeth inside a patient's mouth that are adjacent to or remote from the patient's tooth to be cut without covering the patient's tooth to be cut:
    f) a plurality of slots in the cutting guide extending from an exterior of the at least one cutting guide into the at least one cutting guide:
    g) each of the plurality of slots having a cross-sectional shape with a narrower exterior between opposing walls and an enlarged interior with a circular cross-sectional shape;
    h) the cross-sectional shape of the plurality of slots having a size and a shape that matches and mates with a cross-sectional profile of the plurality of guide pins and with the cylindrical shape of the enlarged head matching and mating with the circular cross-sectional shape of the enlarged interior; and i) the plurality of guide pins being slidable in the plurality of slots to guide the cutting burr with respect to the patient's tooth to be cut, the plurality of slots defining a remote cutting path for the cutting burr corresponding to, but remote from, and actual cutting path of the cutting burr on the patient's tooth to be cut, such that displacing the plurality of guide pins along the plurality of slot displaces the cutting burr along the cutting path to cut and shape the patient's tooth to be cut form a cut tooth in a predetermined shape and size.

* * * * *